United States Patent
Hendrix et al.

(10) Patent No.: US 8,088,769 B2
(45) Date of Patent: Jan. 3, 2012

(54) CYANOPYRIMIDINONES

(75) Inventors: Martin Hendrix, Odenthal (DE); Lars Bärfacker, Oberhausen (DE); Heike Heckroth, Odenthal (DE); Dagmar Karthaus, Solingen (DE); Adrian Tersteegen, Wuppertal (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 839 days.

(21) Appl. No.: 10/586,501

(22) PCT Filed: Dec. 31, 2004

(86) PCT No.: PCT/EP2004/014872
§ 371 (c)(1),
(2), (4) Date: Sep. 14, 2007

(87) PCT Pub. No.: WO2005/068436
PCT Pub. Date: Jul. 28, 2005

(65) Prior Publication Data
US 2008/0255118 A1    Oct. 16, 2008

(30) Foreign Application Priority Data
Jan. 14, 2004 (DE) .......................... 10 2004 001 873

(51) Int. Cl.
A61K 31/519 (2006.01)
C07D 487/04 (2006.01)

(52) U.S. Cl. ................ 514/235.8; 514/252.14; 514/269; 544/122; 544/295; 544/326; 544/328

(58) Field of Classification Search .................. 544/122, 544/295, 326, 328; 514/235.8, 252.14, 269
See application file for complete search history.

(56) References Cited

U.S. PATENT DOCUMENTS

| | | | |
|---|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,732,225 A | 5/1973 | Breuer et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,256,668 A | 10/1993 | Hsu et al. |
| 5,270,315 A | 12/1993 | Belleau |
| 5,294,612 A | 3/1994 | Bacon et al. |
| 5,466,806 A | 11/1995 | Belleau et al. |
| 5,541,187 A | 7/1996 | Bacon et al. |
| 5,563,049 A | 10/1996 | Kojima et al. |
| 5,656,629 A | 8/1997 | Bacon et al. |
| 5,684,164 A | 11/1997 | Belleau et al. |
| 5,750,673 A | 5/1998 | Martin |
| 5,969,116 A | 10/1999 | Martin |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,067,507 B2 | 6/2006 | Pulley et al. |
| 7,122,693 B2 | 10/2006 | Belleau et al. |
| 7,488,733 B2 | 5/2007 | Hendrix et al. |
| 7,615,558 B2 | 11/2009 | Hendrix |
| 7,737,156 B2 | 6/2010 | Boss et al. |
| 2001/0041797 A1 | 11/2001 | Belleau et al. |
| 2001/0044441 A1 | 11/2001 | Campbell et al. |
| 2002/0058635 A1 | 5/2002 | Averett |
| 2002/0132754 A1 | 9/2002 | Boss et al. |
| 2003/0087918 A1 | 5/2003 | Belleau et al. |
| 2004/0185459 A1 | 9/2004 | Otsuka et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0209251 A1 | 9/2005 | Linker et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2006/0258651 A1 | 11/2006 | Linschoten et al. |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2009/0111838 A1 | 4/2009 | Hendrix et al. |
| 2010/0035900 A1 | 2/2010 | Hendrix et al. |
| 2010/0210839 A1 | 8/2010 | Boss et al. |
| 2011/0015193 A1 | 1/2011 | Eickmeier et al. |
| 2011/0065730 A1 | 3/2011 | Hendrix et al. |
| 2011/0082137 A1 | 4/2011 | Giovannini et al. |

FOREIGN PATENT DOCUMENTS

CA    1 311 201    12/1992
(Continued)

OTHER PUBLICATIONS

F. Josef van der Staay, et al., "The novel selective PDE9 inhibitor BAY 73-6691 improves learning and memory in rodents", Neuropharmacology, 55 (2008) pp. 908-916. U. Ebert, et al., "Scopolamine model of dementia: electroencephalogram findings and cognitive performance", European Journal of Clinical Investigation, (1998) 28, pp. 944-949.
Jos Prickaerts, et al., "Possible role of nitric oxide-cyclic GMP pathway in object recognition memory: Effect of 7-nitroindazole and zaprinast", European Journal of Pharmacology 337 (1997) pp. 125-136.
F. Zaragoza Dörwald, "Side Reactions in Organic Synthesis", A Guide to Successful Systhesis Design, 2005, 4 pages.
Kenneth F. Podraza, "Reductive Cyclization of Ketoesters Utilizing Sodium Cyanoborohydride: Synthesis of γ- and δ-Lactones" J. Heterocyclic Chem., 24, 193 (1987).
Internet Article, "Amnesia", From Wikipedia, the free encyclopedia, 3 pages, (2008).

(Continued)

Primary Examiner — Deepak Rao
(74) Attorney, Agent, or Firm — Michael P. Morris; Edward S. Lazer

(57) ABSTRACT

The invention relates to novel cyanopyrimidinones, process for their preparation, and the use thereof for producing medicaments for improving perception, concentration, learning and/or memory.

6 Claims, No Drawings

FOREIGN PATENT DOCUMENTS

| | | |
|---|---|---|
| CA | 2 283 211 A1 | 9/1998 |
| CA | 2 438 890 A1 | 9/2002 |
| CA | 2 417 631 A1 | 1/2003 |
| CA | 2 484 997 A1 | 4/2003 |
| CA | 2 466 824 | 5/2003 |
| CA | 2 496 194 | 3/2004 |
| CA | 2 496 194 A1 | 3/2004 |
| CA | 2 496 292 A1 | 4/2004 |
| CA | 2 496 308 A1 | 4/2004 |
| CH | 396 924 | 8/1965 |
| CH | 396 925 | 8/1965 |
| CH | 396 923 | 1/1966 |
| CH | 396 924 | 1/1966 |
| CH | 396 925 | 1/1966 |
| CH | 396 926 | 1/1966 |
| CH | 396 927 | 1/1966 |
| CH | 398 626 | 3/1966 |
| DE | 1 147 234 | 4/1963 |
| DE | 1 149 013 | 5/1963 |
| DE | 1 153 023 | 8/1963 |
| DE | 1 156 415 | 10/1963 |
| DE | 2 408 906 | 9/1974 |
| DE | 4 004 558 | 9/1990 |
| DE | 101 56 249 | 5/2003 |
| DE | 102 38 722 | 3/2004 |
| EP | 0 130 735 | 1/1985 |
| EP | 0130735 A | 1/1985 |
| EP | 0 286 028 | 10/1988 |
| EP | 496 617 | 7/1992 |
| EP | 0 626 387 | 11/1994 |
| EP | 0 679 657 | 11/1995 |
| EP | 0 995 751 A2 | 4/2000 |
| EP | 1 460 077 | 9/2004 |
| GB | 937 723 | 9/1963 |
| GB | 937 724 | 9/1963 |
| GB | 937726 | 9/1963 |
| GB | 973361 | 10/1964 |
| JP | 11-501923 | 2/1999 |
| JP | 2001 514638 | 9/2001 |
| JP | 2002 523507 | 7/2002 |
| JP | 2004 536933 | 12/2004 |
| JP | 2005 531549 | 10/2005 |
| JP | 2006 201272 | 1/2006 |
| JP | 2006 503051 | 1/2006 |
| WO | WO-94 14802 | 7/1994 |
| WO | WO-94 17803 | 8/1994 |
| WO | WO 95/10506 A | 4/1995 |
| WO | WO-97 16456 | 5/1997 |
| WO | WO-97 46569 | 12/1997 |
| WO | WO-98 00434 | 1/1998 |
| WO | WO 98/10765 | 3/1998 |
| WO | WO-98 16184 | 4/1998 |
| WO | WO-98 40384 | 9/1998 |
| WO | WO 98/40384 | 9/1998 |
| WO | WO 99/41253 | 8/1999 |
| WO | WO 00/18758 A | 4/2000 |
| WO | WO-00 043394 | 7/2000 |
| WO | WO-01 05758 | 1/2001 |
| WO | WO-01 60315 | 8/2001 |
| WO | WO-01 77075 | 10/2001 |
| WO | WO 02/06288 A1 | 1/2002 |
| WO | WO 02/09713 A2 | 2/2002 |
| WO | WO-02 16348 | 2/2002 |
| WO | WO 02/055082 A1 | 7/2002 |
| WO | WO-02 057425 | 7/2002 |
| WO | WO 02/068423 A1 | 9/2002 |
| WO | WO-02 074774 | 9/2002 |
| WO | WO-02 086160 | 10/2002 |
| WO | WO 02/098864 A | 12/2002 |
| WO | WO-03 011925 | 2/2003 |
| WO | WO-03 022859 | 3/2003 |
| WO | WO-03 037432 | 5/2003 |
| WO | WO 03/037899 A1 | 5/2003 |
| WO | WO-03 041725 A2 | 5/2003 |
| WO | WO-03 072757 | 9/2003 |
| WO | WO 03/093269 A2 | 11/2003 |
| WO | WO-03 099840 | 12/2003 |
| WO | WO-2004 002999 | 1/2004 |
| WO | WO 2004/018474 A1 | 3/2004 |
| WO | WO 2004/026286 A1 | 4/2004 |
| WO | WO 2004/026286 A2 | 4/2004 |
| WO | WO 2004/026286 A3 | 4/2004 |
| WO | WO 2004/026876 A1 | 4/2004 |
| WO | WO-2004 046331 | 6/2004 |
| WO | WO-2004 096811 | 11/2004 |
| WO | WO-2004 099210 | 11/2004 |
| WO | WO-2004 099211 | 11/2004 |
| WO | WO-2004 108139 | 12/2004 |
| WO | WO-2004 113306 | 12/2004 |
| WO | WO-2005 051944 | 6/2005 |
| WO | WO-2006 076455 | 7/2006 |
| WO | WO-2006 084281 | 8/2006 |
| WO | WO-2006 091905 | 8/2006 |
| WO | WO-2006 125548 | 11/2006 |
| WO | WO-2007 025043 | 3/2007 |
| WO | WO-2007 046747 | 4/2007 |
| WO | WO-2008 005542 | 1/2008 |
| WO | WO-2008 055959 | 5/2008 |
| WO | WO-2008 100447 | 8/2008 |
| WO | WO-2008 104077 | 9/2008 |
| WO | WO-2008 139293 | 11/2008 |
| WO | WO-2009 068617 | 6/2009 |
| WO | WO-2009 121919 | 10/2009 |
| WO | WO-2010 026214 | 3/2010 |
| WO | WO-2010 112437 | 10/2010 |
| WO | WO-2011 018495 | 2/2011 |

OTHER PUBLICATIONS

Reid IA, "Role of phosphodiesterase isoenzymes in the control of rennin secretion: effects of selective enzyme inhibitors", Curr Pharm Des, Sep. 1999; 5(9); 725-35.

Edwin J. Weeber, et al., "Molecular Genetics of Human Cognition", Molecular Inventions, vol. 2, Issue 6, Oct. 2002, pp. 376-391.

International Search Report for International Application No. PCT/EP2004/004455 mailed Sep. 17, 2004, 8 pages.

International Search Report for International Application No. PCT/EP2004/004412 mailed Jul. 14, 2004, 6 pages.

International Search Report for International Application No. PCT/EP03/08979 mailed Nov. 25, 2003, 8 pages.

International Search Report for International Application No. PCT/EP03/08923 mailed Dec. 15, 2003, 6 pages.

International Search Report for International Application No. PCT/EP2004/006477 mailed Oct. 27, 2004, 8 pages.

International Search Report for International Application No. PCT/EP2004/014872 mailed May 19, 2005, 10 pages.

Scott H. Soderling, et al., "Identification and Characterization of a Novel Family of Cyclic Nucleotide Phosphodiesterases", The Journal of Biological Chemistry, vol. 273, No. 25, Issue of Jun. 19, 1998, pp. 15553-15558.

Scott H. Soderling, et al., "Regulation of cAMP and cGMP signaling: new phosphodiesterases and new functions", Current Opinion in Cell Biology, 2000, 12:174-179.

Svetlana G. Andreeva, et al., "Expression of cGMP-Specific Phosphodiesterase 9A mRNA in the Rat Brain", The Journal of Neuroscience, Nov. 15, 2001, 21(22); pp. 9068-9076.

C. C. Cheng, et al., "Potential Purine Antagonist VII. Synthesis of 6-Alkylpyrazolo-[3,4-d]pyrimidines$^{12a}$", Potential Purine Antagonists, VII, vol. 23, Feb. 1958, pp. 191-200.

Lindsay Fawcett, et al., "Molecular cloning and characterization of a distance human phosphodiesterase gene family: PDE11A", PNAS, vol. 97, No. 7, Mar. 28, 2000, pp. 3702-3707.

Douglas A. Fisher, et al., "Isolation and Characterization of PDE9A, a Novel Human cGMP-specific Phosphodiesterase", The Journal of Biological Chemistry, vol. 273, No. 25, Issue of Jun. 19, 1998, pp. 15559-15564.

Douglas A. Fisher, et al., "Isolation and Characterization of PDE8A, a Novel Human cAMP-Specific Phosphodiesterase", Biochemical and Biophysical Research Communications, vol. 246, Apr. 15, 1998, pp. 570-577.

Sharron H. Francais, et al., "Characterization of a Novel cGMP Binding Protein from Rat Lung", The Journal of Biological Chemistry, vol. 255, No. 2, Issue of Jan. 25, 1980, pp. 620-626.

Kotomi Fujishige, et al., "Cloning and Characterization of a Novel Human Phosphodiesterase That Hydrolyzes Both cAMP and cGMP (PDE10A)", The Journal of Biological Chemistry, vol. 274, No. 26, Issue of Jun. 25, 1999, pp. 18438-18445.

Heike Gielen, et al., "A novel approach to amidines from esters", Tetrahedron Letters, 43, 2002, pp. 419-421.

Rudolf Gompper, et al., "Substituted dithiocarboxylic acids and ketene thioacteals", Carboxylic Acid Derivatives, vol. 95, 1962, pp. 2861-2870.

Peter G. Gillespie, et al., "Characterization of a Bovine Cone Photoreceptor Phosphodiesterase Purified by Cyclic GMP-Sepharose Chromatography", The Journal of Biological Chemistry, vol. 263, No. 17, Issue of Jun. 15, 1988, pp. 8133-8141.

Michel Guipponi, et al., "Identification and characterization of a novel cyclic nucleotide phosphodiesterase gene (PDE9A) that maps to 21q22.3: alternative splicing of mRNA transcripts, genomic structure and sequence", Hum Genet (1998) 103:386-392.

J.M. Hetman, et al., "Cloning and characterization of PDE7B, a cAMP-specific phosphodiesterase", PNAS, vol. 97, No. 1, Jan. 4, 2000, pp. 472-476.

Kate Loughney, et al., "Isolation and Characterization of cDNAs Corresponding to Two Human Calcium, Calmodulin-regulated, 3',5'-Cyclic Nucleotide Phosphodiesterases", The Journal of Biological Chemistry, vol. 271, No. 2, Issue of Jan. 12, 1996, pp. 796-806.

James E. Huettner, et al., "Primary Culture of Identified Neurons from the Visual Cortex of Postnatal Rats", The Journal of Neuroscience, vol. 6, No. 10, pp. 3044-3060, (1986).

Kate Loughney, et al., "Isolation and characterization of cDNAs encoding PDE5A, a human cGMP-binding, cGMP-specific 3',5'-cyclic nucleotide phosphodiesterase", Gene, 216 (1998), pp. 139-147.

Clair Lugnier, "Cyclic nucleotide phosphodiesterasse (PDE) superfamily: A new target for the development of specific therapeutic agents", Pharmacology & Therapeutics, 109 (2006), pp. 366-398.

Timothy J. Martins, et al., "Purification and Characterization of a Cyclic GMP-stimulated Cyclic Nucleotide Phoshoiesterase from Bovine Tissues", The Journal of Biological Chemistry, vol. 257, No. 4, Issue of Feb. 25, 1981, pp. 1973-1979.

Akira Miyashita, et al. "Studies on Pyrazolo[3,4-d]Pyrimidine Derivatives", Heterocycle, vol. 31, No. 7, 1990, pp. 1309-1314.

Takashi Miki, et al., "Characterization of the cDNA and Gene Encoding Human PDE3B, the cGIP1 Isoform of the Human Cyclic GMP-Inhibited Cyclic Nucleotide Phosphodiesterase Family", Genomics, 36, 1996, pp. 476-485.

Seiko Murashima, et al., "Characterization of Particulate Cyclic Nucleotide Phosphodiesterases from Bovine Brain: Purification of a Distinct cGMP-Stimulated Isognzyme," Biochemistry, vol. 29, 1990, pp. 5285-5292.

Rena Obernotle, et al., "The cDNA of a human lymphocyte cyclic-AMP phosphodiesterase (PDE IV) reveals a multigene family", Gene, vol. 29, 1993, pp. 239-247.

K. Hemender Reddy, et al., "Versatile synthesis of 6-alkyl/aryl-1H-pyrazolo[3,4-d]pyrimidin-4[5H]-ones", Indian Journal of Chemistry, vol. 31B, Mar. 1992, pp. 163-166.

Magnus Roenn, et al., "Palladium (II)-Catalyzed Cyclization Using Molecular Oxygen as Reoxidant", Tetrahedron Letters, vol. 36, No. 42, 1995, pp. 7749-7752.

Guy J. Rosman, et al., "Isolation and Characterization of human cDNAs encoding a cGMP-stimulated 3',5'-cyclic nucleotide phosphodiesterase", Gene, vol. 191, 1997, pp. 89-95.

P. Schmidt, et al., "A new synthesis of pyrazolo [3,4-d] pyrimidines having coronary dilation properties", Helvetica Chimica Acta, vol. XLV, fascicule V (1962) No. 189, pp. 1620-1627.

Arne Schousboe, et al., "Role of CA$^{++}$ and Other Second Messengers in Excitatory Amino Acid Receptor Mediated Neurodegeneration: Clinical Perspectives", Clinical Neuroscience, vol. 4, 1997, pp. 194-198.

Joachim Ulirch, "Crystallization", Kirk-Othmer Encyclopedia of Chemical Technology, Aug. 16, 2002, 7 pages.

Anthony R. West, "Solid Solutions", Department of Chemistry University of Aberdeen, Mar. 3, 1988, 3 pages.

Sudha R. Vippagunta, et al., "Crystalline Solids", Advanced Drug Delivery Reviews, vol. 48, 2001, pp. 3-26.

Ji-Ye Wei, et al., "Molecular and Pharmacological Analysis of Cyclic Nucleotide-Gated Channel Function in the Central Nervous System", Progress in Nueorobiology, vol. 56, 1998, pp. 37-64.

Internet Article, "Dementia", Information from the Mental Health Foundation, Mar. 19, 2008, 3 pages.

Jehan Bagli, Chemistry and Positive Inotropic Effect of Pelrinone and Related Derivatives. A Novel Class of 2-Methylpyrimidones as Inotropic Agents, J. Med. Chem., 1988, pp. 814-823, 31(4).

Frank Wunder, et al. "Characterization of the First Potent and Selective PDE9 Inhibitor Using a cGMP Reporter Cell Line" Molecular Pharmacology, 68(6) :1775-1781, (2005).

Wang et al., "Insight into binding of phosphodiesterase-9-A selective inhibitors by crystal structures and mutagenesis," J. Med. Chem., Oct. 12, 2009.

Deninno et al., "The discovery of potent, selective, and orally bioavailable PDE9 inhibitors as potential hypoglycemic agents," Bioorganic & Medicinal Chemistry Letters, 2009, vol. 9, pp. 2537-2541.

Hendrix et al., "Use of Pyrazolopyrimidine Against Cardiovascular Disease," Publication Date: Nov. 30, 2006, Data Supplied from the espacenet database Worldwide; English Abstract of WO 2006125548.

Hendrix et al., "6-cyclymethyl-and 6-alkylmethyl-Substituted Pyrazolopyrimidines," Publication Date: Nov. 18, 2004, Data Supplied from the espacenet database Worldwide; English Abstract of WO 2004099211.

Wunder et al., "Characterization of the first potent and selective PDE9 inhibitor using a cGMP Reporter Cell Line," Molecular Pharmacology, 2005, vol. 68, pp. 1775-1781.

Accessed on Dec. 18, 2008, http://en.wikipedia.org/wiki/Amnesia.

Accessed on Dec. 18, 2008, www.mentalhealth.org.uk/information/mental-health-a-z/dementia.

Barger et al., "Role of cyclic GMP in the Regulation of Neuronal Calcium and Survival by Secreted Forms of Beta-Amyloid Precursor," J of Neurochem, 1995, vol. 64, No. 5, pp. 2087-2096.

Byrn et al., Solid State Chemistry of Drugs, 1999, Second Edition, Chapter 11, pp. 232-247.

Chem Abstracts Service, Database Accession No. ALB-H01677136, Database Chemcats, 2007, XP002556399.

Francis et al., "Cortical Pyramidal Neurone Loss May Cause Glutamaterigic Hypoactivity and Cognitive Impairment in Alzheimer's Disease: Investigative and Therapeutic Perspectives," Journal of Neurochemistry,1993, vol. 60, No. 5, pp. 1589-1604.

Francis et al., "Glutamatergic systems in Alzheimer's disease," International Journal of Geriatric Psychology, 2003, vol. 18, p. S15-21.

Harb et al., "Pyrazoles as building blocks in heterocyclic synthesis . . . " Chemical Papers, 2005, vol. 59, No. 3, pp. 187-195, XP002498868.

Hendrix, M. et al., "Use of pyrazolopyrimidine against cardiovascular diseases," Data retrieved from espacenet worldwide database, Publication Date: Nov. 30, 2006; English Abstract of WO-2006 125548.

Hetman et al., "Isolation and characterization of PDE7B, a . . . " Proc. Nat. Acad. Sci., 2000, vol. 97, No. 1, pp. 472-476.

Hung et al., "A high-yielding synthesis of monalkylhydrazines," Journal of Organic Chemistry, 1981, vol. 46, pp. 5413-5414.

International Search Report of PCT/EP2003/08880 dated Apr. 1, 2004, International Filing Date: Aug. 11, 2003, International Publication No. WO 2004 026286.

Last accessed Jul. 15, 2010 http://www.nlm.nih.gov/medlineplus/ency/article/000746.htm.

Markwalder, J. A. et al., "Synthesis and Biological Evaluation of 1-Aryl-4,5-dihydro-1 H-pyrazolo[3,4-d]pyrimidin-4-one Inhibitors of Cyclin-Dependent Kinases," J of Med Chemistry, 2004, vol. 47, pp. 5894-5911, XP002399637.

Prickaerts et al., "Effects of two selective phosphodiesterase type 5 inhibitors, sildenafil and vardenafil, on object recognition memory and hippocampal cyclic gmp levels in the rat," Neuroscience, 2002, vol. 113, No. 2, pp. 351-361.

Puzzo et al., "Amyloid-Beta Peptide Inhibits Activation of the Nitric Oxide/Cgmp/Camp-Responsive Element-Binding Protein Pathway during Hippocampal Synaptic Plasticity," The Journal of Neuroscience, 2005, vol. 25, No. 29, pp. 6887-6897.

Related U.S. Appl. No. 12/855,129, filed Aug. 12, 2010.
Related U.S. Appl. No. 12/935,686, filed Sep. 30, 2010.
Related U.S. Appl. No. 13/062,625, filed Mar. 7, 2011.
Related U.S. Appl. No. 13/099,064, filed May 2, 2011.
Reymann et al., "The late maintenance of hippocampal LTP: Requirements, phases, 'synaptic tagging', 'late-associativity' and implications," Neuropharmacology, 2007, vol. 52, pp. 24-40.
Skipper et al., "Structure-Activity Relationships Observed on Screening a Series of Pyrazolopyrimidines against Experimental Neoplasms," Cancer Research, 1957, vol. 17, pp. 579-596.
Timberlake et al., "Chemistry of Hydrazo-, Azo-, and Azoxy Groups," Patai, 1975, Chapter 4.
Ugarkar et al., "Synthesis and antiviral/antitumor activities of . . . ," Journal of Medicinal Chemistry, 1984, vol. 27, No. 8, pp. 1026-1030.
Van Staveren et al., Journal of Neurocytology, 2002, vol. 31, pp. 729-741.
Wang et al., "Identification and characterization of a new human type 9 Cgmp-specific phosphodiesterase-splice variant (PDE9A5) Different tissue distribution and subcellular localization of PDE9A variants," Gene, 2003, vol. 214 pp. 15-27.

CYANOPYRIMIDINONES

This application is a 371 of PCT/EP2004/014872, filed Dec. 31, 2004.

The invention relates to novel cyanopyrimidinones, process for their preparation, and the use thereof for producing medicaments for improving perception, concentration, learning and/or memory.

Inhibition of phosphodiesterases modulates the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., Prog. Neurobiol., 1998, 56: 37-64). The phosphodiesterases (PDE) are a control mechanism for controlling the activity of cAMP and cGMP and thus in turn these physiological processes. PDEs hydrolyze the cyclic monophosphates to the inactive monophosphates AMP and GMP. At least 21 PDE genes have now been described (Exp. Opin. Investig. Drugs 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letter (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 μM). PDE9A has no cGMP binding domain, suggesting allosteric enzyme regulation by cGMP. It was shown in a Western blot analysis that PDE9A is expressed in humans inter alia in the testes, brain, small intestine, skeletal muscle, heart, lung, thymus and spleen. The highest expression was found in the brain, small intestine, heart and spleen (Fisher et al., J. Biol. Chem., 1998, 273 (25): 15559-15564). The gene for human PDE9A is located on chromosome 21q22.3 and comprises 21 exons. To date, 4 alternative splice variants of PDE9A have been identified (Guipponi et al., Hum. Genet., 1998, 103: 386-392). Classical PDE inhibitors do not inhibit human PDE9A. Thus, IBMX, dipyridamole, SKF94120, rolipram and vinpocetine show no inhibition on the isolated enzyme in concentrations of up to 100 μM. An $IC_{50}$ of 35 μM has been demonstrated for zaprinast (Fisher et al., J. Biol. Chem., 1998, 273 (25): 15559-15564).

Murine PDE9A was cloned and sequenced in 1998 by Soderling et al. (J. Biol. Chem., 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 μM either; the $IC_{50}$ for zaprinast is 29 μM (Soderling et al., J. Biol. Chem., 1998, 273 (19): 15553-15558). It has been found that PDE9A is strongly expressed in some regions of the rat brain. These include olfactory bulb, hippocampus, cortex, basal ganglia and basal forebrain (Andreeva et al., J. Neurosci., 2001, 21 (22): 9068-9076). The hippocampus, cortex and basal forebrain in particular play an important role in learning and memory processes.

As already mentioned above, PDE9A is distinguished by having particularly high affinity for cGMP. PDE9A is therefore active even at low physiological concentrations, in contrast to PDE2A (Km=10 μM; Martins et al., J. Biol. Chem., 1982, 257: 1973-1979), PDE5A (Km=4 μM; Francis et al., J. Biol. Chem., 1980, 255: 620-626), PDE6A (Km=17 μM; Gillespie and Beavo, J. Biol. Chem., 1988, 263 (17): 8133-8141) and PDE11A (Km=0.52 μM; Fawcett et al., Proc. Nat. Acad. Sci., 2000, 97 (7): 3702-3707). In contrast to PDE2A (Murashima et al., Biochemistry, 1990, 29: 5285-5292), the catalytic activity of PDE9A is not increased by cGMP because it has no GAF domain (cGMP-binding domain via which the PDE activity is allosterically increased) (Beavo et al., Current Opinion in Cell Biology, 2000, 12: 174-179). PDE9A inhibitors may therefore lead to an increase in the baseline cGMP concentration.

U.S. Pat. No. 5,002,949 discloses cyanopyrimidinones for inhibiting white thrombus formations.

WO 02/06288 describes cyanopyrimidinones having mGluR antagonistic effect.

WO 95/10506 discloses cyanopyrimidinones for the treatment of depression and Alzheimer's disease.

EP 130735 describes cyanopyrimidines as cardiotonic reagents.

U.S. Pat. No. 5,256,668 and WO 99/41253 disclose cyanopyrimidines having an antiviral effect.

The present invention relates to compounds of the formula

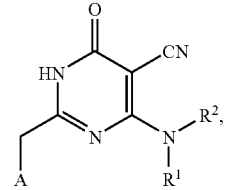
(I)

in which
A is phenyl, heteroaryl or a group of the formula

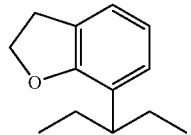

where phenyl and heteroaryl are optionally substituted by up to 2 radicals independently of one another selected from the group of heteroaryl, halogen, $C_1$-$C_6$-alkyl, $C_1$-$C_6$-alkoxy, trifluoromethyl, trifluoromethoxy, benzyloxy and benzyl,
where $C_1$-$C_6$-alkyl is optionally substituted by a group of the formula —$NR^3R^4$ in which $R^3$ is $C_1$-$C_6$-alkyl and $R^4$ is hydrogen or $C_1$-$C_6$-alkoxy($C_1$-$C_6$)alkyl, and heteroaryl is optionally substituted by $C_1$-$C_6$-alkoxy, $R^1$ is $C_3$-$C_8$-cycloalkyl, $C_1$-$C_6$-alkyl, $C_1$-$C_6$-alkoxy($C_1$-$C_6$) alkyl, benzyl or a group of the formula

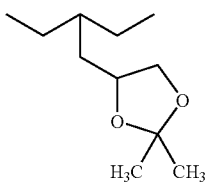

where $C_3$-$C_8$-cycloalkyl is optionally substituted by hydroxy, $C_1$-$C_6$-alkyl or trifluoromethyl,
$C_1$-$C_6$-alkyl is optionally substituted by heteroaryl, $C_3$-$C_8$-cycloalkyl or hydroxy,
and benzyl is optionally substituted by $C_1$-$C_6$-alkoxy or halogen,
$R^2$ is hydrogen,
or
$R^1$ and $R^2$ together with the nitrogen atom to which they are bonded form a 5- to 6-membered heterocyclyl which is optionally substituted by up to 2 substituents independently of one another selected from the group of $C_1$-$C_6$-alkyl, hydroxy, cyano, oxo, heteroaryl, benzyl, formyl, $C_1$-$C_6$-alkylcarbonyl and one of the following groups

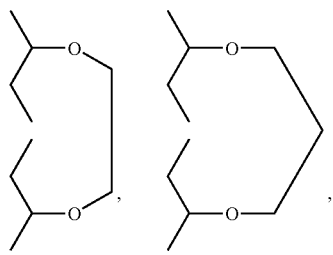

which are linked via the two oxygen atoms to one of the carbon atoms in the heterocycle,
where $C_1$-$C_6$-alkyl is optionally substituted by hydroxy or heteroaryl,
and the salts, solvates and/or solvates of the salts thereof.

The compounds of the invention may, depending on their structure, exist in stereoisomeric forms (enantiomers, diastereomers) and tautomeric forms. The invention therefore relates to the enantiomers or diastereomers and respective mixtures thereof. The stereoisomerically pure constituents can be isolated in a known manner from such mixtures of enantiomers and/or diastereomers.

Salts which are preferred for the purposes of the invention are physiologically acceptable salts of the compounds of the invention.

Physiologically acceptable salts of the compounds (I) include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, tri-ethanolamine, dicyclohexylamine, dimethylaminoethanol, procaine, dibenzylamine, N-methylmorpholine, dehydroabietylamine, arginine, lysine, ethylenediamine and methylpiperidine.

Solvates refers for the purposes of the invention to those forms of the compounds which form, in the solid or liquid state, a complex by coordination with solvent molecules. Hydrates are a specific form of solvates in which the coordination takes place with water.

For the purposes of the present invention, the substituents have the following meaning, unless specified otherwise:

$C_1$-$C_6$-alkyl is a straight-chain or branched alkyl radical having 1 to 6, preferably 1 to 4 carbon atoms. Preferred examples include methyl, ethyl, n-propyl, isopropyl, 2-butyl, tert-butyl, 2-pentyl, 3-pentyl and n-hexyl.

$C_1$-$C_6$-alkoxy is a straight-chain or branched alkoxy radical having 1 to 6, preferably 1 to 4, particularly preferably having 1 to 3 carbon atoms. Preferred examples include methoxy, ethoxy, n-propoxy, isopropoxy, tert-butoxy, n-pentoxy and n-hexoxy.

$C_1$-$C_6$-alkoxy($C_1$-$C_6$ alkyl is a straight-chain or branched alkoxy radical having 1 to 6, preferably 1 to 4, particularly preferably having 1 to 3 carbon atoms, which is linked to a straight-chain or branched alkyl radical having 1 to 6, preferably 1 to 4, particularly preferably having 2 to 3 carbon atoms. Preferred examples include methoxymethyl, 2-methoxyethyl, ethoxymethyl and 2-ethoxyethyl.

$C_1$-$C_6$-alkylcarbonyl is a straight-chain or branched alkylcarbonyl radical having 1 to 6, preferably 1 to 4 and particularly preferably 1 to 3 carbon atoms. Preferred examples include methylcarbonyl, ethylcarbonyl, n-propylcarbonyl, isopropylcarbonyl and tert-butylcarbonyl.

3- to 8-membered cycloalkyl is saturated cycloalkyl radicals having 3 to 8, preferably 3 to 6 and particularly preferably 5 to 6 carbon atoms in the ring. Preferred examples include cyclopropyl, cyclobutyl, cyclopentyl, cyclohexyl and cycloheptyl.

Halogen is fluorine, chlorine, bromine and iodine. Fluorine, chlorine, bromine are preferred, and fluorine and chlorine are particularly preferred.

Heteroaryl is an aromatic, monocyclic radical having 5 to 6 ring atoms and up to 3 heteroatoms from the series S, O and/or N. 5- to 6-membered heteroaryls having up to 2 heteroatoms are preferred. The heteroaryl radical may be bonded via a carbon or nitrogen atom. Preferred examples include thienyl, furyl, pyrrolyl, thiazolyl, oxazolyl, imidazolyl, pyridyl, pyrimidinyl and pyridazinyl.

5- to 6-membered heterocyclyl is a monocyclic, saturated or partially unsaturated heterocyclic radical having 5 to 6 ring atoms and up to 2 heteroatoms from the series N, O, S, N and O are preferred as heteroatoms. Preferred examples include pyrrolidinyl, pyrrolinyl, tetrahydrofuranyl, tetrahydrothienyl, pyranyl, thiopyranyl, piperidinyl, morpholinyl, thiomorpholinyl and piperazinyl. When radicals in the compounds of the invention are optionally substituted, unless otherwise specified substitution by up to three identical or different substituents is preferred.

A further embodiment of the invention relates to compounds of the formula (I) in which A is phenyl, heteroaryl or a group of the formula

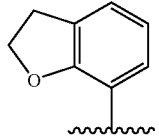

where phenyl and heteroaryl are optionally substituted by up to 2 radicals independently of one another selected from the group of heteroaryl, halogen, $C_1$-$C_4$-alkyl, $C_1$-$C_4$-alkoxy, trifluoromethyl, trifluoromethoxy, benzyloxy and benzyl,
where $C_1$-$C_4$-alkyl is optionally substituted by a group of the formula —$NR^3R^4$ in which $R^3$ is $C_1$-$C_4$-alkyl and $R^4$ is hydrogen or $C_1$-$C_4$-alkoxy($C_1$-$C_4$)alkyl, and
heteroaryl is optionally substituted by $C_1$-$C_4$-alkoxy, $R^1$ is $C_3$-$C_6$-cycloalkyl, $C_1$-$C_4$-alkyl, $C_1$-$C_4$-alkoxy($C_1$-$C_4$)alkyl, benzyl or a group of the formula

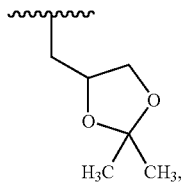

where $C_3$-$C_6$-cycloalkyl is optionally substituted by hydroxy, $C_1$-$C_4$-alkyl or trifluoromethyl,
$C_1$-$C_4$-alkyl is optionally substituted by heteroaryl, $C_3$-$C_6$-cycloalkyl or hydroxy,
and benzyl is optionally substituted by $C_1$-$C_4$-alkoxy or halogen, $R^2$ is hydrogen,
or
$R^1$ and $R^2$ together with the nitrogen atom to which they are bonded form a 5- to 6-membered heterocyclyl which is optionally substituted by up to 2 substituents independently of one another selected from the group of $C_1$-$C_4$-alkyl, hydroxy, cyano, oxo, heteroaryl, benzyl, formyl, $C_1$-$C_4$-alkylcarbonyl and one of the following groups

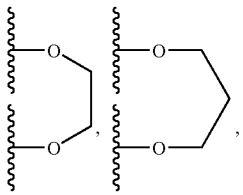

which are linked via the two oxygen atoms to one of the carbon atoms in the heterocycle,
where $C_1$-$C_4$-alkyl is optionally substituted by hydroxy or heteroaryl,
and the salts, solvates and/or solvates of the salts thereof.

A further embodiment of the invention relates to compounds of the formula (I) in which A is phenyl, thienyl or a group of the formula

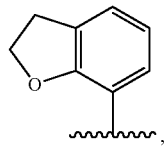

where phenyl and thienyl are optionally substituted by up to 2 radicals independently of one another selected from the group of pyridyl, fluorine, chlorine, bromine, $C_1$-$C_4$-alkyl, $C_1$-$C_4$-alkoxy, trifluoromethyl, trifluoromethoxy, benzyloxy and benzyl,
where $C_1$-$C_4$-alkyl is optionally substituted by a group of the formula —$NR^3R^4$ in which $R^3$ is $C_1$-$C_4$-alkyl and $R^4$ is hydrogen or $C_1$-$C_4$-alkoxy($C_1$-$C_4$)alkyl, and
pyridyl is optionally substituted by $C_1$-$C_4$-alkoxy, $R^1$ is $C_3$-$C_6$-cycloalkyl, $C_1$-$C_4$-alkyl, $C_1$-$C_4$-alkoxy($C_1$-$C_4$)alkyl, benzyl or a group of the formula

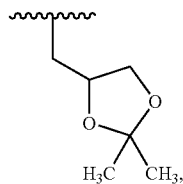

where $C_3$-$C_6$-cycloalkyl is optionally substituted by hydroxy, $C_1$-$C_4$-alkyl or trifluoromethyl,
$C_1$-$C_4$-alkyl is optionally substituted by pyridyl, $C_3$-$C_6$-cycloalkyl or hydroxy,
and benzyl is optionally substituted by $C_1$-$C_4$-alkoxy, fluorine, chlorine or bromine, $R^2$ is hydrogen,
or
$R^1$ and $R^2$ together with the nitrogen atom to which they are bonded form a 5- to 6-membered heterocyclyl selected from the group of pyrrolidinyl, piperidinyl, piperazinyl and morpholinyl, which is optionally substituted by up to 2 substituents independently of one another selected from the group of $C_1$-$C_4$-alkyl, hydroxy, cyano, oxo, heteroaryl, benzyl, formyl, $C_1$-$C_4$-alkylcarbonyl and one of the following groups

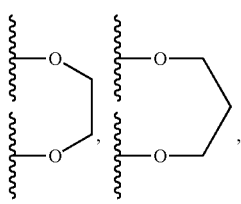

which are linked via the two oxygen atoms to one of the carbon atoms in the heterocycle,
where $C_1$-$C_4$-alkyl is optionally substituted by hydroxy or pyridyl,
and the salts, solvates and/or solvates of the salts thereof.

A further embodiment of the invention relates to compounds of the formula (I) in which
A is phenyl, thienyl or a group of the formula

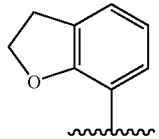

where phenyl is optionally substituted by up to 2 radicals independently of one another selected from the group of pyridyl, fluorine, chlorine, methyl, methoxy, ethoxy, trifluoromethyl, trifluoromethoxy, benzyloxy and benzyl, where methyl is optionally substituted by a group of the formula —$NR^3R^4$ in which $R^3$ is methyl and $R^4$ is hydrogen or 2-methoxyethyl, and
pyridyl is optionally substituted by methoxy,
$R^1$ is $C_3$-$C_6$-cycloalkyl, methyl, ethyl, propyl, 2-methoxyethyl, benzyl or a group of the formula

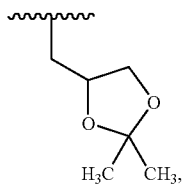

where $C_3$-$C_6$-cycloalkyl is optionally substituted by hydroxy, methyl or trifluoromethyl,
methyl, ethyl, propyl is optionally substituted by pyridyl, cyclopropyl or hydroxy,
and benzyl is optionally substituted by methoxy, ethoxy, fluorine or chlorine,
$R^2$ is hydrogen,
or
$R^1$ and $R^2$ together with the nitrogen atom to which they are bonded form a 5- to 6-membered heterocyclyl selected from the group of pyrrolidinyl, piperidinyl, piperazinyl and morpholinyl, which is optionally substituted by up to 2 substituents independently of one another selected from the group of methyl, ethyl, propyl, tert-butyl, hydroxy, cyano, oxo, pyridyl, benzyl, formyl, methylcarbonyl, ethylcarbonyl, propylcarbonyl and one of the following groups

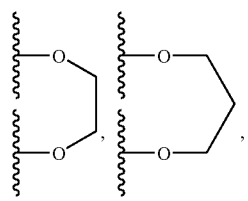

which are linked via the two oxygen atoms to one of the carbon atoms in the heterocycle,
where methyl, ethyl and propyl are optionally substituted by hydroxy or pyridyl,
and the salts, solvates and/or solvates of the salts thereof.

A process for preparing the compounds of the invention of the formula (I) has additionally been found, characterized in that either

[A] a compound of the formula

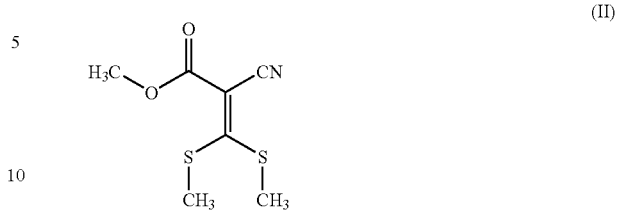

is initially converted with a compound of the formula
$$HNR^1R^2 \qquad (III)$$
in which
$R^1$ and $R^2$ have the abovementioned meanings,
at elevated temperature in an inert solvent or else in the absence of a solvent into a compound of the formula

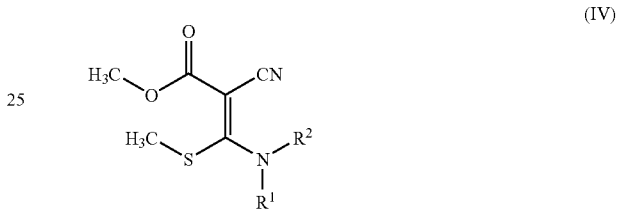

in which
$R^1$ and $R^2$ have the abovementioned meanings,
and the latter is then reacted in an inert solvent in the presence of a base with a compound of the formula

in which
A has the abovementioned meanings,
or in a modified sequence of the reactants
[B] a compound of the formula (II) is initially converted with a compound of the formula (V) in an inert solvent in the presence of a base into a compound of the formula

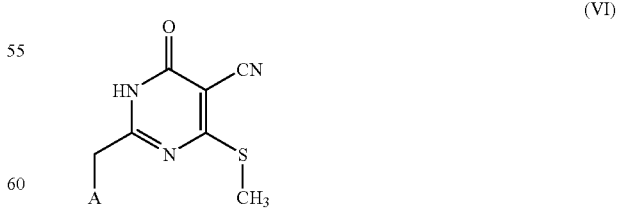

in which
A has the abovementioned meanings,
and the latter is then reacted at elevated temperature in an inert solvent or else in the absence of a solvent with a compound of the formula (III), and the compounds of the formula (I) resulting in each case are reacted where appropriate with the appropriate (i) solvents and/or (ii) bases or acids to give their solvates, salts and/or solvates of the salts.

The compound of the formula (II) is known from the literature (R. Gompper, W. Toepfl, Chem. Ber. 1962, 95, 2861-2870). The compounds of the formulae (III) and (V) are commercially available, known from the literature or can be prepared in analogy to processes known from the literature (see, for example, H. Gielen, C. Alonso-Alija, M. Hendrix, U. Niewöhner, D. Schauss, Tetrahedron Lett. 2002, 43, 419-421).

Solvents suitable for process step (II)+(III)→(IV) are high-boiling, inert organic solvents which are not changed under the reaction conditions. These preferably include toluene, acetonitrile, dimethylformamide, dimethyl sulphoxide or sulpholane. It is likewise possible to carry out the reaction without solvent in the melt. The reaction is particularly preferably carried out without solvent or in dimethylformamide, acetonitrile or toluene.

The reaction generally takes place in a temperature range from +70° C. to +200° C., preferably in a temperature range from +100° C. to +150° C. The reaction can be carried out under atmospheric, elevated or reduced pressure (e.g. from 0.5 to 5 bar). It is generally carried out under atmospheric pressure.

The compound of the formula (III) is in this case employed in an amount of from 1 to 2 mol, preferably in an equivalent amount of 1 mol, based on 1 mol of the compound of the formula (II).

Solvents suitable for process step (VI)+(III)→(I) are the usual organic solvents which are not changed under the reaction conditions. These preferably include dimethylformamide, dimethyl sulphoxide or acetonitrile. It is likewise possible to carry out the reaction without solvent. The reaction is particularly preferably carried out without solvent or in acetonitrile.

The reaction generally takes place in a temperature range from +50° C. to +150° C., preferably in a temperature range from +70° C. to +100° C. The reaction can be carried out under atmospheric, elevated or reduced pressure (e.g. from 0.5 to 5 bar). It is generally carried out under atmospheric pressure.

The compound of the formula (III) is in this case employed in an amount of from 1 to 10 mol, preferably in an excess of from 3 to 10 mol, based on 1 mol of the compound of the formula (VI).

Solvents suitable for process step (IV)+(V)→(I) or (II)+(V)→(VI) are the usual organic solvents which are not changed under the reaction conditions. These preferably include dimethylformamide, dimethyl sulphoxide, acetonitrile, dioxane or alcohols such as methanol, ethanol, propanol, isopropanol, n-butanol or tert-butanol. It is likewise possible to employ mixtures of the solvents mentioned. Dimethylformamide or acetonitrile is particularly preferred for process step (IV)+(V)→(I), and ethanol for process step (II)+(V)→(VI).

The reaction generally takes place in a temperature range from +50° C. to +150° C., preferably in a temperature range from +70° C. to +100° C. The reaction can be carried out under atmospheric, elevated or reduced pressure (e.g. from 0.5 to 5 bar). It is generally carried out under atmospheric pressure.

Bases suitable for process step (IV)+(V)→(I) or (II)+(V)→(VI) are preferably alkali metal carbonates such as lithium, sodium, potassium or caesium carbonate or organic amine bases such as, for example, pyridine, triethylamine, ethyldi-isopropylamine, N-methylmorpholine or N-methyl-piperidine. Potassium carbonate or triethylamine is particularly preferred.

The base is in this case employed in an amount of from 1.5 to 4 mol, preferably in an amount of from 1.5 to 2 mol, based on 1 mol of the compound of the formula (IV) or (II). The compound of the formula (V) is employed in an amount of from 1 to 1.5 mol, preferably in an amount of 1.2 mol, based on 1 mol of the compound of the formula (IV) or (II).

The process of the invention can be illustrated by way of example by the following formula schemes:

Scheme I:

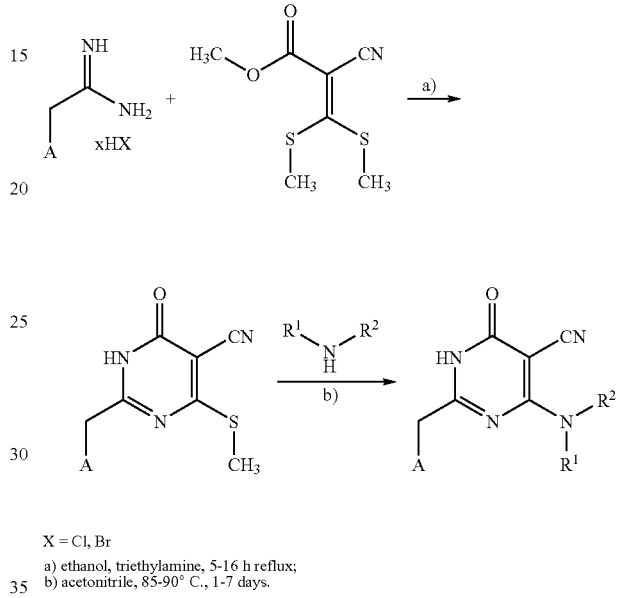

X = Cl, Br
a) ethanol, triethylamine, 5-16 h reflux;
b) acetonitrile, 85-90° C., 1-7 days.

Scheme II:

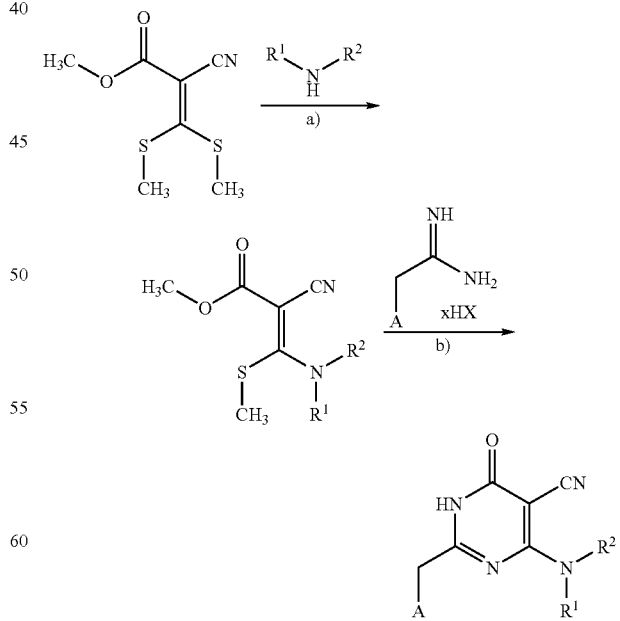

X = Cl, Br
a) 1. toluene, boron trifluoride-etherate, RT, 30 min.; 2. Amine component $R^1R^2NH$, 150° C., 16 h; or: melt of the starting compounds at 150° C., 1-16 h; b) DMF, triethylamine, 100° C., 16 h or DMF, potassium carbonate, 90° C., 16 h.

The compounds of the invention show a valuable range of pharmacological effects which could not have been predicted. They are distinguished in particular by inhibition of PDE9A.

It has surprisingly been found that the compounds of the invention are suitable for producing medicaments for improving perception, concentration, learning or memory.

The compounds of the invention can, by reason of their pharmacological properties, be employed alone or in combination with other medicaments for improving perception, concentration, learning and/or memory.

The compounds of the invention are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

The in vitro effect of the compounds of the invention can be shown with the following biological assays:

PDE Inhibition

Recombinant PDE1C (GenBank/EMBL Accession Number: NM_005020, Loughney et al. *J. Biol. Chem.* 1996 271, 796-806), PDE2A (GenBank/EMBL Accession Number: NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene.* 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472-476), PDE8A (GenBank/EMBL Accession Number: AF_056490, Fisher et al. *Biochem. Biophys. Res. Commun.* 1998, 246, 570-577), PDE9A (Fisher et al., J. Biol. Chem., 1998, 273 (25): 15559-15564), PDE10A (GenBank/EMBL Accession Number: NM_06661, Fujishige et al. *J Biol Chem.* 1999, 274, 18438-45), PDE11A (GenBank/EMBL Accession Number: NM_016953, Fawcett et al. *Proc. Natl. Acad. Sci.* 2000, 97, 3702-3707) were expressed in Sf9 cells with the aid of the pFASTBAC baculovirus expression system (GibcoBRL).

The test substances are dissolved in 100% DMSO and serially diluted to determine their in vitro effect on PDE9A. Typically, serial dilutions from 200 µM to 1.6 µM are prepared (resulting final concentrations in the assay: 4 µM to 0.032 µM). 2 µl portions of the diluted substance solutions are introduced into the wells of microtitre plates (Isoplate; Wallac Inc., Atlanta, Ga.). Then 50 µl of a dilution of the PDE9A preparation described above are added. The dilution of the PDE9A preparation is chosen so that less than 70% of the substrate is converted during the subsequent incubation (typical dilution: 1:10 000; dilution buffer: 50 mM Tris/HCl pH 7.5, 8.3 mM MgCl$_2$, 1.7 mM EDTA, 0.2% BSA). The substrate, [8-$^3$H]guanosine 3',5'-cyclic phosphate (1 µCi/µl; Amersham Pharmacia Biotech., Piscataway, N.J.) is diluted 1:2000 with assay buffer (50 mM Tris/HCl pH 7.5, 8.3 mM MgCl$_2$, 1.7 mM EDTA) to a concentration of 0.0005 µCi/µl.

The enzyme reaction is finally started by adding 50 µl (0.025 µCi) of the diluted substrate. The assay mixtures are incubated at room temperature for 60 min and the reaction is stopped by adding 25 µl of a PDE9A inhibitor (e.g. the inhibitor from Preparation Example 1, final concentration 10 µM) dissolved in assay buffer. Immediately thereafter, 25 µl of a suspension containing 18 mg/ml Yttrium Scintillation Proximity Beads (Amersham Pharmacia Biotech., Piscataway, N.J.) are added. The microtitre plates are sealed with a film and left to stand at room temperature for 60 min. The plates are then measured for 30 s per well in a Microbeta scintillation counter (Wallac Inc., Atlanta, Ga.). IC$_{50}$ values are determined from the graphical plot of the substance concentration versus the percentage inhibition.

The in vitro effect of test substances on recombinant PDE3B, PDE4B, PDE7B, PDE8A, PDE10A and PDE11A is determined by the assay protocol described above for PDE9A with the following adaptations: the substrate used is [5',8-$^3$H] adenosine 3',5'-cyclic phosphate (1 µCi/µl; Amersham Pharmacia Biotech., Piscataway, N.J.). Addition of an inhibitor solution to stop the reaction is unnecessary. Instead, the incubation of substrate and PDE is followed directly by addition of the Yttrium Scintillation Proximity Beads as described above, and the reaction is stopped thereby. To determine a corresponding effect on recombinant PDE1C, PDE2A and PDE5A, the protocol is additionally adapted as follows: in the case of PDE1C, additionally calmodulin 10$^{-7}$ M and CaCl$_2$ 3 mM are added to the reaction mixture. PDE2A is stimulated in the assay by adding cGMP 1 µM and assayed using a BSA concentration of 0.01%. The substrate employed for PDE1C and PDE2A is [5',8-$^3$H]adenosine 3',5'-cyclic phosphate (1 µCi/µl; Amersham Pharmacia Biotech., Piscataway, N.J.) and for PDE5A is [8-$^3$H]guanosine 3',5'-cyclic phosphate (1 µCi/µl; Amersham Pharmacia Biotech., Piscataway, N.J.).

Representative examples of the PDE9A-inhibiting effect of the compounds of the invention are listed in Tables 1 to 3 on the basis of the IC$_{50}$ values.

Tables 1-3: Inhibition of PDE isoenzymes (human) by Examples 38, 112 and 113

TABLE 1

Example 38

| Isoenzyme | IC$_{50}$ [nM] |
|---|---|
| PDE1C | >4000 |
| PDE2A | >4000 |
| PDE3B | >4000 |
| PDE4B | >4000 |
| PDE7B | 2200 |
| PDE8A | 4000 |
| PDE9A | 5 |
| PDE10A | >4000 |
| PDE11 | >4000 |

TABLE 2

Example 112

| Isoenzyme | IC$_{50}$ [nM] |
|---|---|
| PDE1C | >4000 |
| PDE2A | >4000 |
| PDE3B | >4000 |
| PDE4B | >4000 |
| PDE7B | >4000 |
| PDE8A | >4000 |

TABLE 2-continued

Example 112

| Isoenzyme | IC$_{50}$ [nM] |
|---|---|
| PDE9A | 5 |
| PDE10A | >4000 |
| PDE11 | >4000 |

TABLE 3

Example 113

| Isoenzyme | IC$_{50}$ [nM] |
|---|---|
| PDE1C | >4000 |
| PDE2A | >4000 |
| PDE3B | >4000 |
| PDE4B | >4000 |
| PDE7B | >4000 |
| PDE8A | >4000 |
| PDE9A | 15 |
| PDE10A | >4000 |
| PDE11 | 1500 |

Long-Term Potentiation

Long-term potentiation is regarded as a cellular correlate of learning and memory processes. The following method can be used to determine whether PDE9 inhibition has an influence on long-term potentiation:

Rat hippocampi are placed at an angle of about 70 degrees to the cutting blade (chopper). 400 µm-thick slices of the hippocampus are prepared. The slices are removed from the blade using a very soft, thoroughly wetted brush (marten hair) and transferred into a glass vessel with cold nutrient solution (124 mM NaCl, 4.9 mM KCl, 1.3 mM MgSO$_4$×7H$_2$O, 2.5 mM CaCl$_2$ anhydrous, 1.2 mM KH$_2$PO$_4$, 25.6 mM NaHCO$_3$, 10 mM glucose, pH 7.4) gassed with 95% O$_2$/5% CO$_2$. During the measurement, the slices are kept in a temperature-controlled chamber under a 1-3 mm-high liquid level. The flow rate is 2.5 ml/min. The preliminary gassing takes place under a slightly elevated pressure (about 1 atm) and through a microneedle in the prechamber. The slice chamber is connected to the prechamber in such a way that a minicirculation can be maintained. The minicirculation is driven by the 95% O$_2$/5% CO$_2$ flowing out through the microneedle. The freshly prepared hippocampus slices are adapted in the slice chamber at 33° C. for at least 1 hour.

The stimulus level is chosen so that the focal excitatory postsynaptic potentials (fEPSP) are 30% of the maximum excitatory postsynaptic potential (EPSP). A monopolar stimulation electrode consisting of lacquered stainless steel, and a constant-current biphasic stimulus generator (AM Systems 2100) are used for local stimulation of the Schaffer collaterals (voltage: 1-5 V, pulse width of one polarity 0.1 ms, total pulse 0.2 ms). Glass electrodes (borosilicate glass with filament, 1-5 MOhm, diameter: 1.5 mm, tip diameter: 3-20 µm), filled with normal nutrient solution, are used to record the excitatory postsynaptic potentials (fEPSP) from the stratum radiatum. The field potentials are measured versus a chlorinated silver reference electrode located at the edge of the slice chamber using a DC voltage amplifier. The field potentials are filtered through a low-pass filter (5 kHz). The slope of the fEPSPs (fEPSP slope) is determined for the statistical analysis of the experiments. The recording, analysis and control of the experiment takes place with the aid of a software program (PWIN) which was developed in the Department of Neurophysiology. The formation of the average fEPSP slopes at the respective time points and construction of the diagrams takes place with the aid of the EXCEL software, with automatic data recording by an appropriate macro.

Superfusion of the hippocampus slices with a 10 µM solution of the compounds of the invention leads to a significant increase in the LTP.

The in vivo effect of the compounds of the invention can be shown for example as follows:

Social Recognition Test

The social recognition test is a learning and memory test. It measures the ability of rats to distinguish between known and unknown members of the same species. This test is therefore suitable for examining the learning- or memory-improving effect of the compounds of the invention.

Adult rats housed in groups are placed singly in test cages 30 min before the start of the test. Four min before the start of the test, the test animal is put in an observation box. After this adaptation time, a juvenile animal is put in with the test animal and the absolute time for which the adult animal inspects the young one is measured for 2 min (trial 1). All behaviours clearly directed at the young animal are measured, i.e. anogenital inspection, pursuit and grooming, during which the old animal was no further than 1 cm from the young animal. The juvenile is then removed, and the adult is treated with a compound of the invention or vehicle and subsequently returned to its home cage. The test is repeated after a retention time of 24 hours (trial 2). A diminished social interaction time compared with trial 1 indicates that the adult rat remembers the young animal.

The adult animals receive intraperitoneal injections either within a defined time period (e.g. 1 hour) before trial 1 or directly following trial 1 either with vehicle (10% ethanol, 20% Solutol, 70% physiological saline) or 0.1 mg/kg, 0.3 mg/kg, 1.0 mg/kg or 3.0 mg/kg compound of the invention dissolved in 10% ethanol, 20% Solutol, 70% physiological saline. Vehicle-treated rats show no reduction in the social interaction time in trial 2 compared with trial 1. They have consequently forgotten that they have already had contact with the young animal. Surprisingly, the social interaction time in the second run after treatment with the compounds of the invention is significantly reduced compared with those treated with vehicle. This means that the substance-treated rats have remembered the juvenile animal and thus the compounds of the invention display an improving effect on learning and memory.

The novel active ingredients can be converted in a known manner into conventional formulations such as tablets, coated tablets, pills, granules, aerosols, syrups, emulsions, suspensions and solutions, by use of inert, non-toxic, pharmaceutically suitable carriers or solvents. In these cases, the therapeutically effective compound is to be present in each case in a concentration of about 0.5 to 90% by weight in the complete mixture, i.e. in amounts which are sufficient to achieve the indicated dosage range.

The formulations are produced for example by diluting the active ingredients with solvents and/or carriers, where appropriate with use of emulsifiers and/or dispersants, it being possible for example in the case where water is used as diluent where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved to be advantageous to administer amounts of about 0.001 to 10, on oral administration preferably about 0.005 to 3, mg/kg of body weight to achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, whereas in other cases the stated upper limit must be exceeded. If larger amounts are administered, it may be advisable to divide these into a plurality of single doses over the day.

Unless indicated otherwise, all stated amounts refer to percentages by weight. Solvent ratios, dilution ratios and concentrations stated for liquid/liquid solutions are based in each case on volume. The statement "w/v" means "weight/volume". Thus, for example, "10% w/v" means 100 ml of solution or suspension contain 10 g of substance.

Abbreviations:
DCI direct chemical ionization (in MS)
DMSO dimethyl sulphoxide
ESI electrospray ionization (in MS)
h hour(s)
HPLC high-pressure, high-performance liquid chromatography
LC-MS coupled liquid chromatography-mass spectroscopy
min minute(s)
m.p. melting point
MS mass spectroscopy
NMR nuclear magnetic resonance spectroscopy
$R_f$ retention index (in TLC)
RT room temperature
$R_t$ retention time (in HPLC)

LC-MS and HPLC Methods:
Method 1:
Instrument: Micromass Platform LCZ with HPLC Agilent series 1100; column: Grom-Sil 120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 2:
Instrument: Micromass Quattro LCZ with HPLC Agilent series 1100; column: Grom-Sil 120ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 3:
Instrument: Micromass Platform LCZ with HPLC Agilent series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 4:
Instrument: Micromass Quattro LCZ with HPLC Agilent series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 208-400 nm.

Method 5:
MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 6:
MS instrument type: Micromass ZQ; HPLC instrument type: HP 1100 series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 7:
MS instrument type: Micromass ZQ; HPLC instrument type: HP 1100 series; UV DAD; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 0% B→2.9 min 70% B→3.1 min 90% B→4.5 min 90% B; oven: 50° C.; flow rate: 0.8 ml/min; UV detection: 210 nm.

Method 8:
MS instrument type: Micromass ZQ; HPLC instrument type: Waters Alliance 2790; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 5% B→2.0 min 40% B→4.5 min 90% B→5.5 min 90% B; flow rate: 0.0 min 0.75 ml/min→4.5 min 0.75 ml/min→5.5 min 1.25 ml/min; oven: 45° C.; UV detection: 210 nm.

Method 9:
MS instrument type: Micromass ZQ; HPLC instrument type: Waters Alliance 2790; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 0% B→0.2 min 0% B→2.9 min 70% B→3.1 min 90% B→4.5 min 90% B; oven: 45° C.; flow rate: 0.8 ml/min; UV detection: 210 nm.

Method 10:
MS instrument type: Micromass ZQ; HPLC instrument type: Waters Alliance 2795; column: Merck Chromolith SpeedROD RP-18e 50 mm×4.6 mm; eluent A: water+500 µl of 50% strength formic acid/l, eluent B: acetonitrile+500 µl of 50% formic acid/l; gradient: 0.0 min 10% B→3.0 min 95% B→4.0 min 95% B; oven: 35° C.; flow rate: 0.0 min 1.0 ml/min→3.0 min 3.0 mil/min→4.0 min 3.0 ml/min; UV detection: 210 nm.

Method 11:
MS instrument type: Micromass ZQ; HPLC instrument type: Waters Alliance 2790; column: Uptisphere C 18 50 mm×2.0 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 12:
Instrument: HP 1100 with DAD detection; column: Kromasil RP-18, 60 mm×2 mm, 3.5 µm; eluent A: 5 ml of HClO$_4$/l of water, eluent B: acetonitrile; gradient: 0 min 2% B→0.5 min 2% B→4.5 min 90% B→6.5 min 90% B; flow rate: 0.75 ml/min; temperature: 30° C.; UV detection: 210 nm.

Method 13:

Instrument: HP 1100 with DAD detection; column: Kromasil RP-18, 125 mm×4 mm, 5 μm; eluent A: 5 ml of HClO$_4$/l of water, eluent B: acetonitrile; gradient: 0 min 2% B→0.5 min 2% B→4.5 min 90% B→6.5 min 90% B; flow rate: 0.75 ml/min; temperature: 30° C.; UV detection: 210 nm.

Starting Compounds:

The amidines required for the following reactions are prepared from the corresponding nitriles or esters by the method of Gielen H., Alonso-Alija C., Hendrix M., Niewöhner U., Schauβ D., *Tetrahedron Lett.* 43, 419-421 (2002).

EXAMPLE 1A 2-(3,4-Dichlorophenyl)ethanamidine hydrochloride

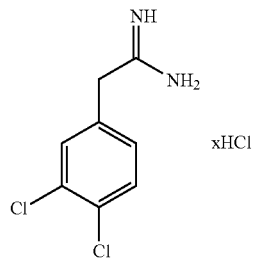

2.88 g (54 mmol) of ammonium chloride are suspended in 50 ml of toluene under an argon atmosphere and cooled to 0° C. After dropwise addition of 27 ml of a 2 M trimethylaluminium solution in toluene, the mixture is warmed to room temperature and then stirred for 1.5 h. 5 g (27 mmol) of 3,4-dichlorophenylacetonitrile are added, and the mixture is stirred at 80° C. overnight. After cooling to 0° C., 50 ml of methanol are added dropwise. The product is separated from the precipitated solid by filtration with suction, and the filter cake is washed several times with methanol. The combined filtrates are evaporated to dryness, and the residue is then suspended in dichloromethane/methanol 10:1 and again filtered with suction. Concentration of the filtrate results in 6.2 g (77% of theory) of the title compound.

MS (ESIpos): m/z=203 [M+H]$^+$.

EXAMPLE 2A

6-Methoxypyridin-3-ylboronic acid

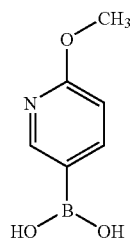

1 g (5.32 mmol) of 5-bromo-2-methoxypyridine is dissolved in 10 ml of absolute tetrahydrofuran and cooled to −78° C. Addition of 0.4 g (6.38 mmol) of a 1.6 M n-butyllithium solution in hexane results in a yellow solution which is stirred at the given temperature for 30 min. Addition of 3 g (15.9 mmol) of triisopropyl borate is followed by stirring for a further hour, during which the solution warms to −20° C. Water is added, and the mixture is stirred overnight. The crude solution is acidified to pH 5 with 1 N hydrochloric acid and extracted twice with ethyl acetate. The organic phase is dried over sodium sulphate, filtered and concentrated, resulting in a pale brown solid which is suspended in diethyl ether and filtered. 0.38 g (47% of theory) of the product is isolated.

MS (ESIpos): m/z=154 [M+H]$^+$ $^1$H-NMR (DMSO-d$_6$, 300 MHz): δ=3.83 (s, 3H), 6.76 (d, 1H), 8.0 (dd, 1H), 8.52 (s, 1H).

EXAMPLE 3A

Methyl[2-(6-methoxypyridin-3-yl)phenyl]acetate

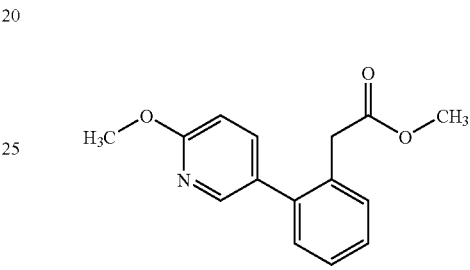

1.35 g (5.89 mmol) of methyl (2-bromophenyl)acetate are introduced together with 1 g (6.55 mmol) of 6-methoxypyridin-3-ylboronic acid and 1.98 g (13.09 mmol) of caesium fluoride into 20 ml of 1,2-dimethoxyethane under argon. After addition of 0.22 g (0.19 mmol) of tetrakis(triphenylphosphine)palladium(0), the reaction mixture is stirred at 100° C. for 4 h. Cooling to room temperature is followed by addition of a mixture of ethyl acetate and water and extraction with ethyl acetate. After the organic phase has been dried over magnesium sulphate and the solvent has been removed in vacuo, the residue is purified by column chromatography on silica gel (mobile phase: cyclohexane/ethyl acetate 9:1). 1.1 g (68% of theory) of the product are obtained.

LC-MS (method 5): R$_t$=2.1 min., MS (ESIpos): m/z=258 [M+H]$^+$ $^1$H-NMR (DMSO-d$_6$, 300 MHz): δ=3.51 (s, 3H), 3.63 (s, 2H), 3.9 (s, 3H), 6.89 (d, 1H), 7.26 (m, 1H), 7.38 (m, 3H), 7.63 (dd, 1H), 8.08 (m, 1H).

EXAMPLE 4A

2-[2-(6-Methoxypyridin-3-yl)phenyl]ethanimidamide hydrochloride

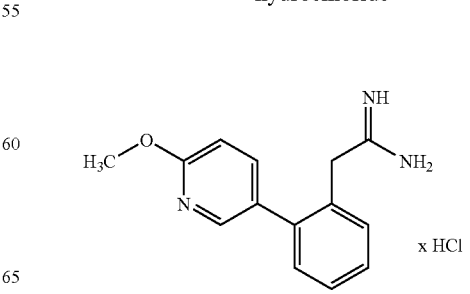

1.14 g (21.37 mmol) of ammonium chloride are suspended in 20 ml of toluene under an argon atmosphere and cooled to 0° C. After dropwise addition of 10.7 ml of a 2 M trimethylaluminium solution in toluene, the mixture is warmed to room temperature and then stirred for 1.5 h. 1.1 g (4.27 mmol) of methyl[2-(6-methoxypyridin-3-yl)phenyl]acetate are added, and the mixture is stirred at 80° C. for two days. After cooling to 5° C., 50 ml of methanol are added dropwise. The product is separated from the precipitated solid by filtration with suction, and the filter cake is washed several times with methanol. The combined filtrates are evaporated to dryness, and the residue is then suspended in dichloromethane/methanol 10:1 and again filtered with suction. Concentration of the filtrate results in 0.5 g (46% of theory) of the title compound.

LC-MS (method 5): $R_t$=0.94 min., MS (ESIpos): m/z=242 [M+H]$^+$ $^1$H-NMR (DMSO-d$_6$, 300 MHz): δ=3.79 (s, 2H), 3.9 (s, 3H), 6.89 (d, 1H), 7.31 (m, 2H), 7.46 (m, 2H), 7.68 (dd, 1H), 8.12 (m, 1H), 8.72 (s, 1H), 8.8 (s, 2H).

EXAMPLE 5A

2-[2-(6-Methoxypyridin-3-yl)benzyl]-4-(methylsulphanyl)-6-oxo-1,6-dihydropyrimidine-5-carbonitrile

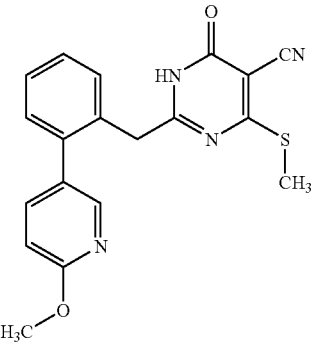

0.55 g (1.96 mmol) of 2-[2-(6-methoxypyridin-3-yl)phenyl]ethanimidamide hydrochloride are dissolved together with 0.4 g (1.96 mmol) of methyl 2-cyano-3,3-dimethylthioprop-2-enoate and 0.79 g (7.81 mmol) of triethylamine in 20 ml of dioxane and stirred at 90° C. overnight. The solvent is then removed in vacuo, apart from about 2 ml, and acetonitrile is added to the remaining solution, whereupon the product precipitates. Filtration is followed by washing with acetonitrile and methanol, and the product is dried under high vacuum. 276 mg (38% of theory) of the title compound are obtained.

LC-MS (method 5): $R_t$=2.08 min., MS (ESIpos): m/z=365 [M+H]$^+$ $^1$H-NMR (DMSO-d$_6$, 300 MHz): δ=2.31 (s, 3H), 3.9 (s, 3H), 3.98 (s, 2H), 6.89 (d, 1H), 7.28 (m, 1H), 7.39 (m, 3H), 7.63 (dd, 1H), 8.08 (m, 1H).

EXAMPLE 6A

2-Benzyl-4-(methylsulphanyl)-6-oxo-1,6-dihydro-5-pyrimidinecarbonitrile

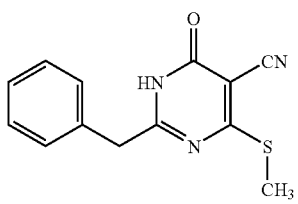

100 mg (0.59 mmol) of 2-phenylethanamidine hydrochloride are dissolved together with 119 mg (0.59 mmol) of methyl 2-cyano-3,3-dimethylthioprop-2-enoate and 237 mg (2.34 mmol) of triethylamine in 2 ml of ethanol and stirred at 70° C. for 5 h. The solvent is then removed in vacuo, and the residue is taken up in 50 ml of dichloromethane and washed with 2 M hydrochloric acid. After the organic phase has been dried over magnesium sulphate, the solvent is removed in vacuo, and the residue is flash-chromatographed on silica gel (mobile phase: dichloromethane/methanol 200:1, 100:1). 75 mg (50% of theory) of the title compound are obtained.

HPLC (method 12): $R_t$=4.2 min.

MS (ESIpos): m/z=258 [M+H]$^+$.

EXAMPLE 7A 2-(3-Methylbenzyl)-4-(methylsulphanyl)-6-oxo-1,6-dihydro-5-pyrimidinecarbonitrile

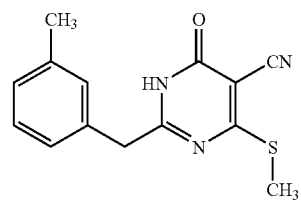

1.45 g (9.83 mmol) of 2-(3-methylphenyl)ethanamidine hydrochloride are dissolved together with 2 g (9.83 mmol) of methyl 2-cyano-3,3-dimethylthioprop-2-enoate and 2 g (19.67 mmol) of triethylamine in 40 ml of ethanol and stirred at 70° C. for 5 h. The solvent is then removed in vacuo, and the residue is purified by preparative HPLC. 0.4 g (15% of theory) of the product is obtained.

LC-MS (method 2): $R_t$=2.83 min., MS (ESIpos): m/z=272 [M+H]$^+$ $^1$H-NMR (DMSO-d$_6$, 300 MHz): δ=2.25 (s, 3H), 2.50 (s, 3H), 3.91 (s, 2H), 7.19 (m, 4H).

EXAMPLE 8A 2-(2-Methylbenzyl)-4-(methylsulphanyl)-6-oxo-1,6-dihydro-5-pyrimidinecarbonitrile

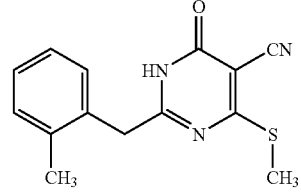

3 g (16.45 mmol) of 2-(2-methylphenyl)ethanamidine hydrochloride are dissolved together with 3.3 g (16.45 mmol) of methyl 2-cyano-3,3-dimethylthioprop-2-enoate and 6.6 g (64.9 mmol) of triethylamine in 60 ml of dioxane and stirred at 90° C. overnight. After removal of the triethylammonium salts by filtration, the filtrate is concentrated and the residue is triturated with dichloromethane. 3.6 g (81% of theory) of the product are obtained.

LC-MS (method 10): $R_t$=2.13 min., MS (ESIpos): m/z=272 [M+H]$^+$.

EXAMPLE 9A 2-(2-Fluorobenzyl)-4-(methylsulphanyl)-6-oxo-1,6-dihydro-5-pyrimidinecarbonitrile

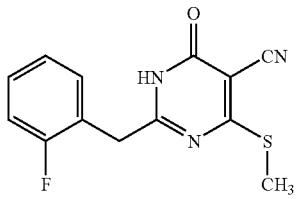

3.5 g (18.5 mmol) of 2-(2-fluorophenyl)ethanamidine hydrochloride are dissolved together with 3.8 g (18.5 mmol) of methyl 2-cyano-3,3-dimethylthioprop-2-enoate and 7.5 g (74.2 mmol) of triethylamine in 50 ml of dioxane and stirred at 90° C. overnight. After removal of the triethylammonium salts by filtration, the filtrate is concentrated and the residue is taken up in ethyl acetate. The product is precipitated by adding 1 N hydrochloric acid and water. 3.8 g (75% of theory) of the title compound are obtained.

LC-MS (method 10): $R_t$=2.03 min., MS (ESIpos): m/z=276 [M+H]$^+$ $^1$H-NMR (DMSO-d$_6$, 300 MHz): δ=2.31 (s, 3H), 4.06 (s, 2H), 7.19 (m, 2H), 7.41 (m, 2H).

EXAMPLE 10A 2-(2-Ethoxybenzyl)-4-(methylsulphanyl)-6-oxo-1,6-dihydro-5-pyrimidinecarbonitrile

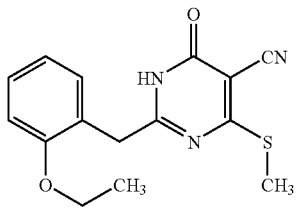

4.2 g (19.7 mmol) of 2-(2-ethoxyphenyl)ethanamidine hydrochloride are dissolved together with 4.0 g (19.7 mmol) of methyl 2-cyano-3,3-dimethylthioprop-2-enoate and 7.9 g (78.7 mmol) of triethylamine in 80 ml of dioxane and stirred at 90° C. overnight. After removal of the triethylammonium salts by filtration, the filtrate is concentrated and the residue is taken up in ethyl acetate. The product is precipitated by adding 1 N hydrochloric acid and water. 5.3 g (90% of theory) of the title compound are obtained.

LC-MS (method 3): $R_t$=2.32 min., MS (ESIpos): m/z=302 [M+H]$^+$ $^1$H-NMR (DMSO-d$_6$, 300 MHz): δ=1.19 (t, 3H), 2.30 (s, 3H), 3.99 (q, 2H+s, 2H), 6.93 (m, 2H), 7.27 (m, 2H).

EXAMPLE 11A 2-(3-Chlorobenzyl)-4-(methylsulphanyl)-6-oxo-1,6-dihydropyrimidine-5-carbonitrile

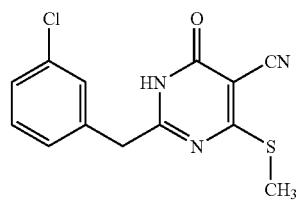

In analogy to the preparation of Example 2A, 0.5 g (2.00 mmol) of 2-(3-chlorophenyl)ethanamidine hydrobromide is reacted with 0.41 g (2.00 mmol) of methyl 2-cyano-3,3-dimethylthioprop-2-enoate and 0.81 g (8.01 mmol) of triethylamine to give 0.5 g (86% of theory) of the title compound.

HPLC (method 12): $R_t$=4.4 min.

MS (DCI, NH$_3$): m/z=292 [M+H]$^+$, 309 [M+NH$_4$]$^+$.

EXAMPLE 12A 2-(4-Chlorobenzyl)-4-(methylsulphanyl)-6-oxo-1,6-dihydropyrimidine-5-carbonitrile

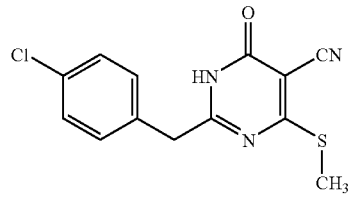

In analogy to the preparation of Example 2A, 10 g (48.8 mmol) of 2-(4-chlorophenyl)ethanamidine hydrochloride are reacted with 9.91 g (48.8 mmol) of methyl 2-cyano-3,3-dimethylthioprop-2-enoate and 19.7 g (195 mmol) of triethylamine to give 7.00 g (49% of theory) of the title compound.

HPLC (method 12): $R_t$=4.35 min.

MS (ESIpos): m/z=292 [M+H]$^+$.

EXAMPLE 13A 2-(3,4-Dichlorobenzyl)-4-(methylsulphanyl)-6-oxo-1,6-dihydropyrimidine-5-carbonitrile

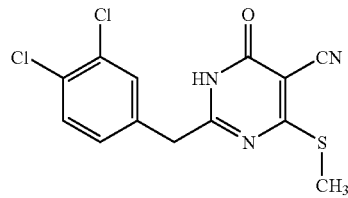

In analogy to the preparation of Example 2A, 1.00 g (4.17 mmol) of 2-(3,4-dichlorophenyl)ethanamidine hydrochloride is reacted with 0.85 g (4.17 mmol) of methyl 2-cyano-3,3-dimethylthioprop-2-enoate and 1.69 g (16.7 mmol) of triethylamine to give 0.6 g (44% of theory) of the title compound.

HPLC (method 12): $R_t$=4.7 min.

MS (DCI, NH$_3$): m/z=343 [M+NH$_4$]$^+$.

EXAMPLE 14A 2-(3-Fluorobenzyl)-4-(methylsulphanyl)-6-oxo-1,6-dihydropyrimidine-5-carbonitrile

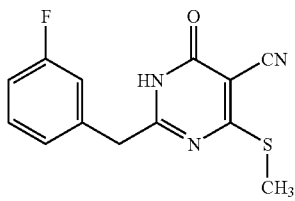

In analogy to the preparation of Example 2A, 100 mg (0.43 mmol) of 2-(3-fluorophenyl)ethanamidine hydrochloride are reacted with 87 mg (0.43 mmol) of methyl 2-cyano-3,3-dimethylthioprop-2-enoate and 174 mg (1.72 mmol) of triethylamine to give 28 mg (24% of theory) of the title compound.

HPLC (method 12): $R_t$=4.2 min.
MS (ESIpos): m/z=276 [M+H]$^+$.

EXAMPLE 15A 4-(Methylsulphanyl)-6-oxo-2-[3-(trifluoromethyl)benzyl]-1,6-dihydropyrimidine-5-carbonitrile

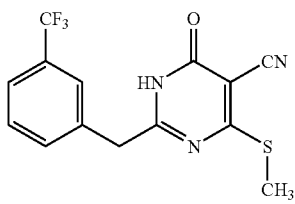

In analogy to the preparation of Example 2A, 0.5 g (2.10 mmol) of 2-[3-(trifluoromethyl)phenyl]-ethanamidine hydrochloride is reacted with 0.43 g (2.10 mmol) of methyl 2-cyano-3,3-dimethylthioprop-2-enoate and 0.85 g (8.38 mmol) of triethylamine to give 0.4 g (59% of theory) of the title compound.

HPLC (method 12): $R_t$=4.4 min.
MS (ESIpos): m/z=326 [M+H]$^+$.

EXAMPLE 16A 4-(Methylsulphanyl)-6-oxo-2-(3-thienylmethyl)-1,6-dihydropyrimidine-5-carbonitrile

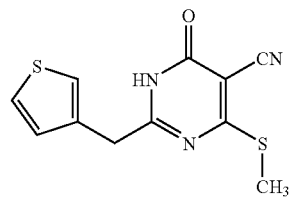

In analogy to the preparation of Example 2A, 3.10 g (17.6 mmol) of 2-(3-thienyl)ethanamidine hydrochloride are reacted with 3.57 g (17.6 mmol) of methyl 2-cyano-3,3-dimethylthioprop-2-enoate and 7.10 g (70.2 mmol) of triethylamine to give 2.19 g (47% of theory) of the title compound.
HPLC (method 12): $R_t$=4.1 min.
MS (ESIpos): m/z=263.9 [M+H]$^+$.

EXAMPLE 17A

Methyl (2E/Z)-2-cyano-3-(cyclohexylamino)-3-methylthioprop-2-enoate

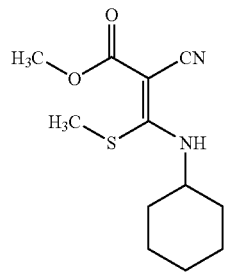

0.6 g (2.9 mmol) of methyl 3,3-bis(methylthio)-2-cyanoacrylate is stirred with 0.29 g (2.9 mmol) of cyclohexylamine in 20 ml of acetonitrile at room temperature for 1 h. The volatile constituents are removed in vacuo. 0.74 g (98% of theory) of the product is obtained as a yellow oil.
HPLC (method 12): $R_t$=4.85 min.
MS (DCI, NH$_3$): m/z=254.9 [M+H]$^+$, 272 [M+NH$_4$]$^+$.

EXAMPLE 18A

Methyl (2E/Z)-2-cyano-3-(cyclopentylamino)-3-methylthioprop-2-enoate

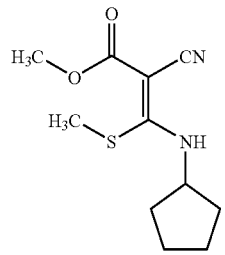

0.3 g (1.47 mmol) of methyl 3,3-bis(methylthio)-2-cyanoacrylate is heated with 0.13 g (1.47 mmol) of cyclopentylamine in 3 ml of acetonitrile at 70° C. for 30 min. The volatile constituents are then removed in vacuo. 0.35 g (98% of theory) of the product is obtained as a yellow oil.

HPLC (method 12): $R_t$=4.6 min.

MS (DCI, NH$_3$): m/z=241 [M+H]$^+$, 258 [M+NH$_4$]$^+$.

Exemplary Embodiments

The following compounds are prepared by the general synthetic route depicted in scheme I:

Scheme I:

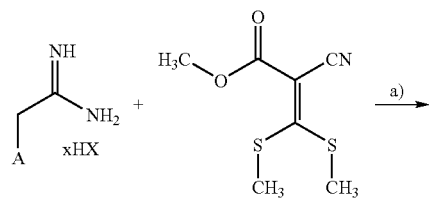

X = Cl, Br
a) ethanol, triethylamine, 5-16 h reflux;
b) acetonitrile, 85-90° C., 1-7 days.

Example 1

2-(3,4-Dichlorobenzyl)-6-oxo-4-(1-piperidinyl)-1,6-dihydropyrimidine-5-carbonitrile

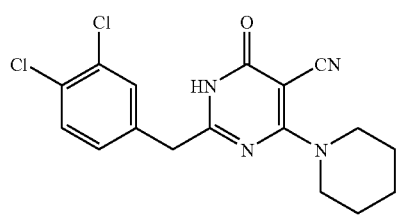

100 mg (0.34 mmol) of 2-(3,4-dichlorobenzyl)-4-(methylsulphanyl)-6-oxo-1,6-dihydropyrimidine-5-carbonitrile are stirred with 261 mg (3.07 mmol) of piperidine at 85° C. for 16 h. After removal of the volatile constituents in vacuo, the residue is purified by preparative HPLC. 42 mg (38% of theory) of the title compound are obtained.

HPLC (method 12): $R_t$=4.8 min.

MS (ESIpos): m/z=363 [M+H]$^+$ $^1$H-NMR (DMSO-d$_6$, 200 MHz): δ=1.45-1.70 (m, 6H), 3.73-3.89 (m, 6H), 7.35 (dd, 1H), 7.57-7.66 (m, 2H), 11.1 (s, 1H).

Example 2

2-Benzyl-6-oxo-4-(1-piperidinyl)-1,6-dihydropyrimidine-5-carbonitrile

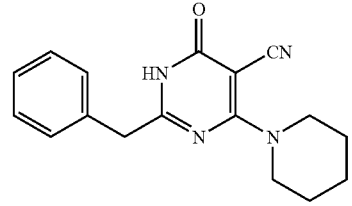

43 mg (0.17 mmol) of 2-benzyl-4-(methylsulphanyl)-6-oxo-1,6-dihydropyrimidine-5-carbonitrile are suspended in 0.3 ml of acetonitrile and stirred with 42.7 mg (0.50 mmol) of piperidine at 85° C. for 16 h. The resulting crude product is then purified by preparative HPLC. 11 mg (22% of theory) of the title compound are obtained.

HPLC (method 12): $R_t$=4.3 min.

MS (ESIpos): m/z=295 [M+H]$^+$ $^1$H-NMR (CD$_3$OD, 300 MHz): δ=1.59-1.77 (m, 6H), 3.83 (s, 2H), 3.93 (t, 4H), 7.24-7.34 (m, 5H).

Example 3

4-[4-(2-Hydroxyethyl)-1-piperidinyl]-2-(3-methylbenzyl)-6-oxo-1,6-dihydro-5-pyrimidinecarbonitrile

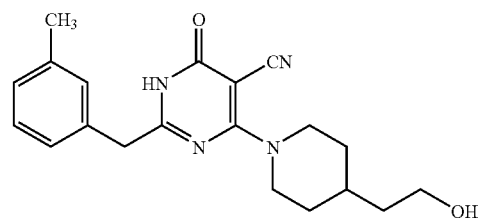

0.1 g (0.37 mmol) of 2-(3-methylbenzyl)-4-(methylsulphanyl)-6-oxo-1,6-dihydro-5-pyrimidinecarbonitrile is heated with 0.142 g (1.16 mmol) of 2-(4-piperidinyl)ethan-1-ol in 3 ml of acetonitrile at 90° C. under argon for seven days. After cooling to room temperature, the crude product is purified by preparative HPLC. 0.047 g (36% of theory) of the title compound is obtained as a colourless solid.

LC-MS (method 7): $R_t$=3.01 min., MS (ESIpos): m/z=353 [M+H]$^+$ $^1$H-NMR (DMSO-d$_6$, 300 MHz): δ=1.05 (m, 2H), 1.36 (m, 2H), 1.69 (m, 3H), 2.25 (s, 3H), 2.89 (t, 2H), 3.42 (t, 2H), 3.68 (s, 2H), 4.51 (d, 2H), 7.18 (m, 4H).

Example 4

4-(Cyclopentylamino)-2-(3-methylbenzyl)-6-oxo-1,6-dihydro-5-pyrimidinecarbonitrile

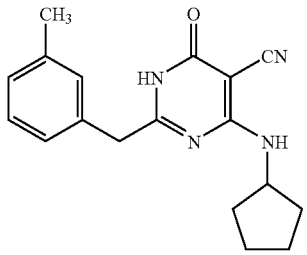

0.1 g (0.37 mmol) of 2-(3-methylbenzyl)-4-(methylsulphanyl)-6-oxo-1,6-dihydro-5-pyrimidinecarbonitrile is heated with 0.31 g (3.65 mmol) of cyclopentylamine in 3 ml of acetonitrile at 90° C. under argon overnight. After cooling to room temperature, the crude product is purified by preparative HPLC. 0.03 g (26% of theory) of the title compound is obtained as a colourless solid.

LC-MS (method 10): $R_t$=2.27 min., MS (ESIpos): m/z=309 [M+H]$^+$.

Example 5

4-[(2S)-2-(Hydroxymethyl)-1-pyrrolidinyl]-2-(3-methylbenzyl)-6-oxo-1,6-dihydro-5-pyrimidinecarbonitrile

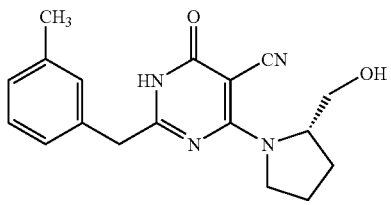

0.1 g (0.37 mmol) of 2-(3-methylbenzyl)-4-(methylsulphanyl)-6-oxo-1,6-dihydro-5-pyrimidinecarbonitrile is heated with 0.11 g (1.1 mmol) of (S)-(+)-2-pyrrolidinemethanol in 3 ml of acetonitrile at 90° C. under argon for five days. After cooling to room temperature, the crude product is purified by preparative HPLC. 0.035 g (29% of theory) of the title compound is obtained as a colourless solid.

LC-MS (method 7): $R_t$=2.91 min., MS (ESIpos): m/z=325 [M+H]$^+$ $^1$H-NMR (DMSO-d$_6$, 300 MHz): δ=1.94 (m, 4H), 2.28 (s, 2H), 3.76 (m, 3H), 3.70 (s, 2H), 3.81 (m, 2H), 4.4 (m, 1H), 7.15 (m, 4H), 12.34 (s, 1H).

Example 6

4-[4-(2-Hydroxyethyl)-1-piperidinyl]-2-(2-methylbenzyl)-6-oxo-1,6-dihydro-5-pyrimidinecarbonitrile

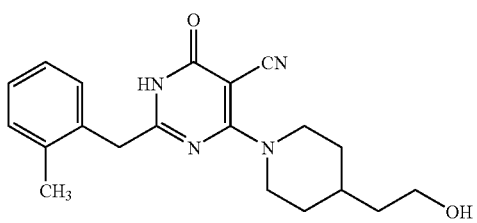

0.1 g (0.37 mmol) of 2-(2-methylbenzyl)-4-(methylsulphanyl)-6-oxo-1,6-dihydro-5-pyrimidinecarbonitrile is heated with 0.14 g (1.1 mmol) of 2-(4-piperidinyl)ethan-1-ol in 3 ml of acetonitrile at 90° C. under argon for five days. After cooling to room temperature, the crude product is purified by preparative HPLC. 13 mg (10% of theory) of the title compound are obtained as a colourless solid.

LC-MS (method 5): $R_t$=1.74 min., MS (ESIpos): m/z=353 [M+H]$^+$ $^1$H-NMR (DMSO-d$_6$, 300 MHz): δ=1.06 (m, 2H), 1.34 (m, 2H), 1.68 (m, 3H), 2.30 (s, 3H), 3.00 (t, 2H), 3.42 (t, 2H), 3.80 (s, 2H), 4.51 (d, 2H), 7.16 (m, 4H), 12.33 (s, 1H).

Example 7

2-(2-Fluorobenzyl)-4-[4-(2-hydroxyethyl)-1-piperidinyl]-6-oxo-1,6-dihydro-5-pyrimidinecarbonitrile

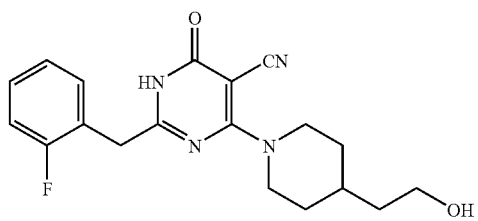

0.1 g (0.37 mmol) of 2-(2-fluorobenzyl)-4-(methylsulphanyl)-6-oxo-1,6-dihydro-5-pyrimidinecarbonitrile is heated with 0.14 g (1.1 mmol) of 2-(4-piperidinyl)ethan-1-ol in 3 ml of acetonitrile at 90° C. under argon for six days. After cooling to room temperature, the crude product is purified by preparative HPLC. 31 mg (24% of theory) of the title compound are obtained as a colourless solid.

LC-MS (method 2): $R_t$=2.94 min., MS (ESIpos): m/z=357 [M+H]$^+$ $^1$H-NMR (DMSO-d$_6$, 300 MHz): δ=1.01 (m, 2H), 1.33 (m, 2H), 1.67 (m, 3H), 2.97 (t, 2H), 3.41 (dd, 2H), 3.87 (s, 2H), 4.32 (t, 1H), 4.47 (d, 2H), 7.16 (m, 2H), 7.36 (m, 2H), 12.38 (s, 1H).

Example 8

2-(2-Ethoxybenzyl)-4-[4-(2-hydroxyethyl)-1-piperidinyl]-6-oxo-1,6-dihydro-5-pyrimidinecarbonitrile

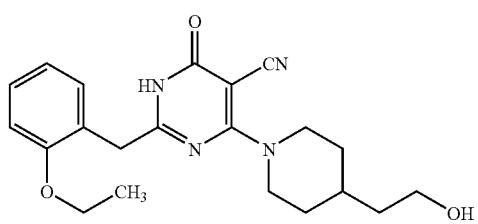

0.1 g (0.37 mmol) of 2-(2-ethoxybenzyl)-4-(methylsulphanyl)-6-oxo-1,6-dihydro-5-pyrimidinecarbonitrile is heated with 0.13 g (0.99 mmol) of 2-(4-piperidinyl)ethan-1-ol in 3 ml of acetonitrile at 90° C. under argon for five days. After cooling to room temperature, the crude product is purified by preparative HPLC. 45 mg (43% of theory) of the title compound are obtained as a colourless solid.

LC-MS (method 6): $R_t$=2.01 min., MS (ESIpos): m/z=383 [M+H]$^+$ $^1$H-NMR (DMSO-d$_6$, 200 MHz): δ=1.04 (m, 2H), 1.23 (t, 3H), 1.34 (m, 2H), 1.67 (m, 3H), 2.94 (t, 2H), 3.41 (t, 2H), 3.87 (s, 2H), 3.96 (q, 2H), 4.48 (d, 2H), 6.92 (m, 2H), 7.17 (m, 2H), 12.26 (s, 1H).

Example 9

2-(3-Chlorobenzyl)-6-oxo-4-(propylamino)-1,6-dihydropyrimidine-5-carbonitrile

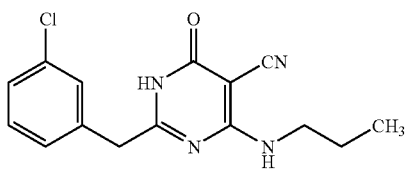

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 203 mg (3.43 mmol) of n-propylamine to give 12 mg (12% of theory) of the title compound.

HPLC (method 12): $R_t$=4.4 min.
MS (ESIpos): m/z=303 [M+H]$^+$
$^1$H-NMR (DMSO-d$_6$, 200 MHz): δ=0.75 (t, 3H), 1.40 (m, 2H), 3.23 (m, 2H), 3.83 (s, 2H), 7.23-7.38 (m, 4H), 7.42 (s, 1H), 12.34 (s, 1H).

Example 10

2-(3-Chlorobenzyl)-4-(cyclopentylamino)-6-oxo-1,6-dihydropyrimidine-5-carbonitrile

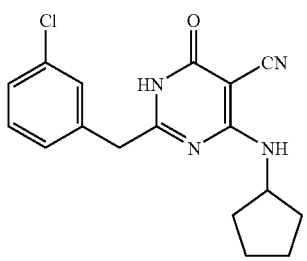

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 292 mg (3.43 mmol) of cyclopentylamine to give 10 mg (9% of theory) of the title compound.

HPLC (method 12): $R_t$=4.6 min.
MS (ESIpos): m/z=329 [M+H]$^+$ $^1$H-NMR (DMSO-d$_6$, 200 MHz): δ=1.38-1.85 (m, 8H), 3.82 (s, 2H), 4.20-4.37 (m, 1H), 7.23-7.46 (m, 4H), 7.66-7.80 (s, 1H), 12.25-12.44 (s, 1H).

Example 11

2-(3-Chlorobenzyl)-6-oxo-4-(1-pyrrolidinyl)-1,6-dihydropyrimidine-5-carbonitrile

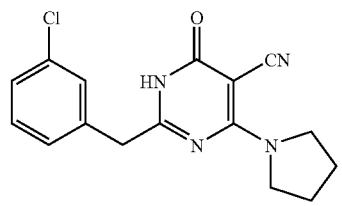

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 244 mg (3.43 mmol) of pyrrolidine to give 29 mg (27% of theory) of the title compound.

HPLC (method 12): $R_t$=4.4 min.
MS (ESIpos): m/z=315 [M+H]$^+$
$^1$H-NMR (DMSO-d$_6$, 200 MHz): δ=1.80-1.95 (m, 4H), 3.58-3.71 (m, 4H), 3.79 (s, 2H), 7.25-7.45 (m, 4H), 12.28-12.39 (s, 1H).

Example 12

4-(4,4-Dimethylpiperidin-1-yl)-2-(3-chlorobenzyl)-6-oxo-1,6-dihydropyrimidine-5-carbonitrile

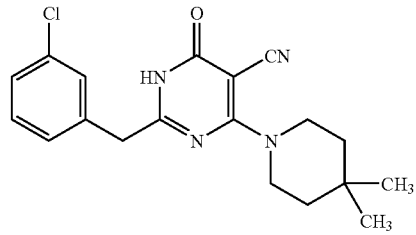

In analogy to the preparation of Example 1, 150 mg (0.51 mmol) of 2-(3-chlorobenzyl)-4-(methylsulphanyl)-6-oxo-1,6-dihydropyrimidine-5-carbonitrile are reacted with 582 mg (5.14 mmol) of 4,4-dimethylpiperidine to give 96 mg (52% of theory) of the title compound.

HPLC (method 12): $R_t$=4.8 min.
MS (ESIpos): m/z=357 [M+H]$^+$ $^1$H-NMR (DMSO-d$_6$, 200 MHz): δ=0.96 (s, 6H), 1.30-1.41 (m, 4H), 3.75-3.87 (m, 6H, s at 3.81), 7.24-7.45 (m, 4H), 12.39 (s, 1H).

Example 13

2-(3-Chlorobenzyl)-4-[(2-methoxyethyl)amino]-6-oxo-1,6-dihydropyrimidine-5-carbonitrile

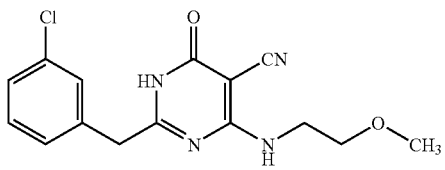

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 257 mg (3.43 mmol) of 2-methoxyethylamine to give 61 mg (56% of theory) of the title compound.

HPLC (method 12): R$_t$=4.0 min.
MS (ESIpos): m/z=319 [M+H]$^+$
$^1$H-NMR (CDCl$_3$, 300 MHz): δ=3.38 (s, 3H), 3.53 (t, 2H), 3.75 (q, 2H), 3.88 (s, 2H), 6.00 (t, 1H), 7.25-7.31 (m, 3H), 7.38 (s, 1H), 12.56 (s, 1H).

Example 14

2-(3-Chlorobenzyl)-4-(morpholin-4-yl)-6-oxo-1,6-dihydropyrimidine-5-carbonitrile

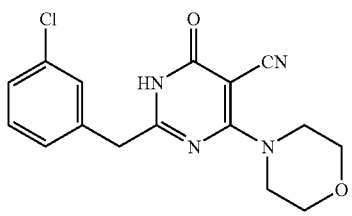

In analogy to the preparation of Example 1, 150 mg (0.51 mmol) of 2-(3-chlorobenzyl)-4-(methylsulphanyl)-6-oxo-1,6-dihydropyrimidine-5-carbonitrile are reacted with 448 mg (5.14 mmol) of morpholine to give 109 mg (63% of theory) of the title compound.

HPLC (method 12): R$_t$=4.0 min.
MS (ESIpos): m/z=331 [M+H]$^+$
$^1$H-NMR (DMSO-d$_6$, 200 MHz): δ=3.59-3.69 (t, 4H), 3.79-3.90 (m, 6H, s at 3.82), 7.25-7.44 (m, 4H), 12.53 (s, 1H).

Example 15

2-(3-Chlorobenzyl)-4-(4-methylpiperazin-1-yl)-6-oxo-1,6-dihydropyrimidine-5-carbonitrile

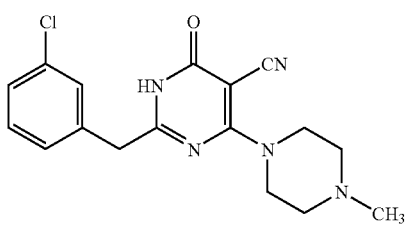

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 343 mg (3.43 mmol) of N-methylpiperazine to give 101 mg (84% of theory) of the title compound.

HPLC (method 12): R$_t$=3.5 min.
MS (ESIpos): m/z=344 [M+H]$^+$
$^1$H-NMR (DMSO-d$_6$, 200 MHz): δ=2.18 (s, 3H), 2.35 (t, 4H), 3.79-3.88 (m, 6H, s at 3.82), 7.25-7.44 (m, 4H), 12.48 (s, 1H).

Example 16

2-(3-Chlorobenzyl)-4-[(2-methoxybenzyl)amino]-6-oxo-1,6-dihydropyrimidine-5-carbonitrile

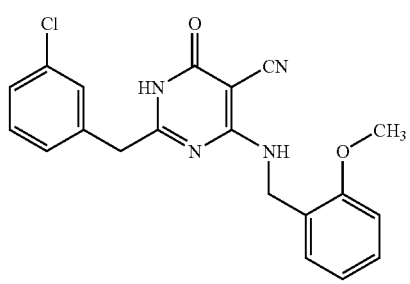

In analogy to the preparation of Example 1, 100 mg (0.34 mmol) of 2-(3-chlorobenzyl)-4-(methylsulphanyl)-6-oxo-1,6-dihydropyrimidine-5-carbonitrile are reacted with 470 mg (3.43 mmol) of 2-methoxybenzylamine to give 37 mg (28% of theory) of the title compound.

HPLC (method 12): R$_t$=4.6 min.
MS (ESIpos): m/z=381 [M+H]$^+$
$^1$H-NMR (DMSO-d$_6$, 300 MHz): δ=3.77 (s, 2H), 3.79 (s, 3H), 4.52 (d, 2H), 6.84 (t, 1H), 6.92-6.99 (m, 2H), 7.12 (d, 1H), 7.19-7.33 (m, 4H), 8.14 (t, 1H), 12.39 (s, 1H).

Example 17

2-(4-Chlorobenzyl)-4-(cyclobutylamino)-6-oxo-1,6-dihydropyrimidine-5-carbonitrile

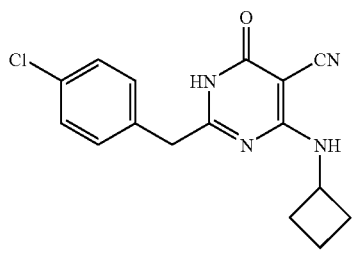

In analogy to the preparation of Example 1, 100 mg (0.34 mmol) of 2-(4-chlorobenzyl)-4-(methylsulphanyl)-6-oxo-1,6-dihydropyrimidine-5-carbonitrile are reacted with 244 mg (3.43 mmol) of cyclobutylamine to give 15 mg (14% of theory) of the title compound.

HPLC (method 12): R$_t$=4.5 min.
MS (ESIpos): m/z=315 [M+H]$^+$

¹H-NMR (DMSO-d₆, 300 MHz): δ=1.50-1.67 (m, 2H), 2.03-2.15 (m, 4H), 3.79 (s, 2H), 4.37-4.51 (m, 1H), 7.31-7.43 (m, 4H), 8.00 (s, 1H), 12.33 (s, 1H).

Example 18

2-(4-Chlorobenzyl)-6-oxo-4-(1-pyrrolidinyl)-1,6-dihydropyrimidine-5-carbonitrile

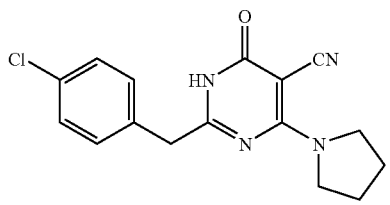

In analogy to the preparation of Example 1, 100 mg (0.34 mmol) of 2-(4-chlorobenzyl)-4-(methylsulphanyl)-6-oxo-1,6-dihydropyrimidine-5-carbonitrile are reacted with 244 mg (3.43 mmol) of pyrrolidine to give 45 mg (42% of theory) of the title compound.

HPLC (method 12): $R_t$=4.4 min.

MS (ESIpos): m/z=315 [M+H]⁺

¹H-NMR (CD₃OD, 300 MHz): δ=1.88-2.03 (m, 4H), 3.69-3.86 (m, 6H, s at 3.82), 7.25-7.35 (m, 4H).

Example 19

4-(Cyclopentylamino)-2-(3-fluorobenzyl)-6-oxo-1,6-dihydropyrimidine-5-carbonitrile

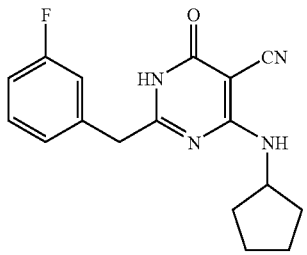

In analogy to the preparation of Example 1, 100 mg (0.36 mmol) of 2-(3-fluorobenzyl)-4-(methylsulphanyl)-6-oxo-1,6-dihydropyrimidine-5-carbonitrile are reacted with 309 mg (3.63 mmol) of cyclopentylamine to give 12 mg (11% of theory) of the title compound.

HPLC (method 12): $R_t$=4.4 min.

MS (ESIpos): m/z=313 [M+H]⁺

¹H-NMR (DMSO-d₆, 200 MHz): δ=1.29-1.71 (m, 8H), 3.89 (s, 2H), 3.98-4.14 (m, 1H), 7.11-7.42 (m, 4H), 7.63-7.75 (s, 1H), 12.34-12.43 (s, 1H).

Example 20

2-(3-Fluorobenzyl)-6-oxo-4-(1-piperidinyl)-1,6-dihydropyrimidine-5-carbonitrile

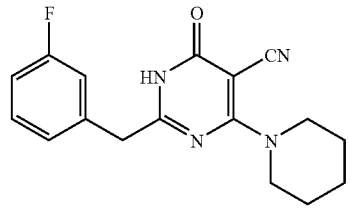

In analogy to the preparation of Example 1, 100 mg (0.36 mmol) of 2-(3-fluorobenzyl)-4-(methylsulphanyl)-6-oxo-1,6-dihydropyrimidine-5-carbonitrile are reacted with 309 mg (3.63 mmol) of piperidine to give 40 mg (35% of theory) of the title compound.

HPLC (method 12): $R_t$=4.3 min.

MS (ESIpos): m/z=313 [M+H]⁺

¹H-NMR (DMSO-d₆, 200 MHz): δ=1.40-1.66 (m, 6H), 3.66-3.76 (m, 4H), 3.76 (s, 2H), 7.12-7.42 (m, 4H), 12.27-12.41 (s, 1H).

Example 21

6-Oxo-4-(1-piperidinyl)-2-[3-(trifluoromethyl)benzyl]-1,6-dihydropyrimidine-5-carbonitrile

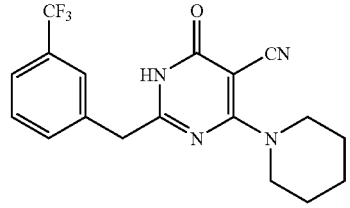

In analogy to the preparation of Example 1, 100 mg (0.31 mmol) of 4-(methylsulphanyl)-6-oxo-2-[3-(trifluoromethyl)benzyl]-1,6-dihydropyrimidine-5-carbonitrile are reacted with 262 mg (3.07 mmol) of piperidine to give 26 mg (22% of theory) of the title compound.

HPLC (method 12): $R_t$=4.7 min.

MS (ESIpos): m/z=363 [M+H]⁺

$^1$H-NMR (DMSO-d$_6$, 200 MHz): δ=1.43-1.70 (m, 6H), 3.71-3.83 (m, 4H), 3.93 (s, 2H), 7.51-7.78 (m, 4H), 12.42 (s, 1H).

Example 22

6-Oxo-4-(propylamino)-2-(3-thienylmethyl)-1,6-dihydropyrimidine-5-carbonitrile

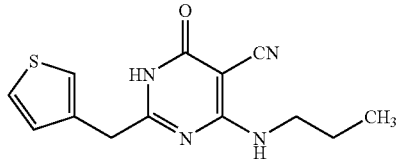

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 224 mg (3.80 mmol) of n-propylamine to give 14 mg (13% of theory) of the title compound.

HPLC (method 12): R$_t$=4.1 min.

MS (ESIpos): m/z=275.2 [M+H]$^+$ $^1$H-NMR (DMSO-d$_6$, 300 MHz): δ=0.79 (t, 3H), 1.46 (m, 2H), 3.29 (m, 2H), 3.81 (s, 2H), 7.06 (d, 1H), 7.33 (s, 1H), 7.49 (m, 1H), 7.87 (s, 1H), 12.27 (s, 1H).

Example 23

4-(Cyclopropylamino)-6-oxo-2-(3-thienylmethyl)-1,6-dihydropyrimidine-5-carbonitrile

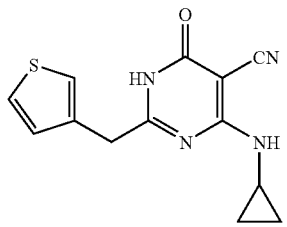

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 217 mg (3.80 mmol) of cyclopropylamine to give 44 mg (43% of theory) of the title compound.

HPLC (method 12): R$_t$=3.8 min.

MS (ESIpos): m/z=273 [M+H]$^+$ $^1$H-NMR (DMSO-d$_6$, 300 MHz): δ=0.60-0.78 (m, 4H), 2.84-2.98 (m, 1H), 3.80 (s, 2H), 7.08 (d, 1H), 7.35 (s, 1H), 7.49 (m, 1H), 7.85-8.05 (s, 1H), 12.32 (s, 1H).

Example 24

4-(Cyclopentylamino)-6-oxo-2-(3-thienylmethyl)-1,6-dihydropyrimidine-5-carbonitrile

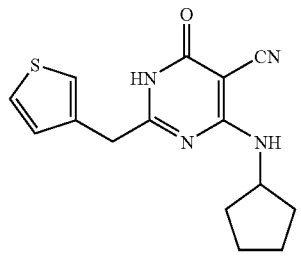

In analogy to the preparation of Example 1, 150 mg (0.57 mmol) of 4-(methylsulphanyl)-6-oxo-2-(3-thienylmethyl)-1,6-dihydropyrimidine-5-carbonitrile are reacted with 485 mg (5.70 mmol) of cyclopentylamine to give 46 mg (26% of theory) of the title compound.

HPLC (method 12): R$_t$=4.4 min.

MS (ESIpos): m/z=301.2 [M+H]$^+$ $^1$H-NMR (DMSO-d$_6$, 300 MHz): δ=1.40-1.91 (m, 8H), 3.81 (s, 2H), 4.36 (m, 1H), 7.07 (d, 1H), 7.34 (s, 1H), 7.50 (m, 1H), 7.65 (s, 1H), 12.28 (s, 1H).

Example 25

6-Oxo-4-(1-pyrrolidinyl)-2-(3-thienylmethyl)-1,6-dihydropyrimidine-5-carbonitrile

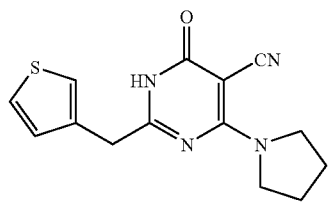

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 270 mg (3.80 mmol) of pyrrolidine to give 64 mg (59% of theory) of the title compound.

HPLC (method 12): R$_t$=4.1 min.

MS (ESIpos): m/z=287 [M+H]$^+$

¹H-NMR (DMSO-d₆, 300 MHz): δ=1.80-1.96 (m, 4H), 3.60-3.76 (m, 4H), 3.78 (s, 2H), 7.08 (d, 1H), 7.35 (s, 1H), 7.48 (m, 1H), 12.27 (s, 1H).

Example 26

4-(4-Methylpiperidin-1-yl)-6-oxo-2-(3-thienylmethyl)-1,6-dihydropyrimidine-5-carbonitrile

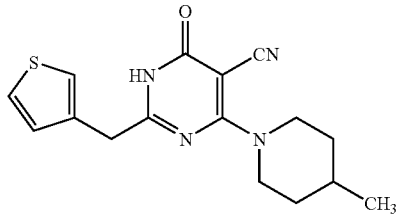

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 377 mg (3.80 mmol) of 4-methylpiperidine to give 65 mg (54% of theory) of the title compound.

HPLC (method 12): R$_t$=4.5 min.
MS (ESIpos): m/z=315 [M+H]⁺
¹H-NMR (DMSO-d₆, 300 MHz): δ=0.91 (d, 3H), 1.05-1.18 (t, 2H), 1.62-1.77 (m, 3H), 3.06 (t, 2H), 3.80 (s, 2H), 4.61 (d, 2H), 7.07 (d, 1H), 7.34 (s, 1H), 7.49 (m, 1H), 12.32 (s, 1H).

Example 27

4-(4,4-Dimethylpiperidin-1-yl)-6-oxo-2-(3-thienylmethyl)-1,6-dihydropyrimidine-5-carbonitrile

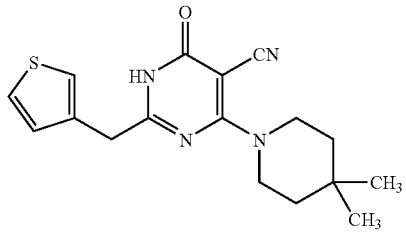

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 430 mg (3.80 mmol) of 4,4-dimethylpiperidine to give 42 mg (34% of theory) of the title compound.

HPLC (method 12): R$_t$=4.6 min.
MS (ESIpos): m/z=329 [M+H]⁺
¹H-NMR (DMSO-d₆, 300 MHz): δ=0.97 (s, 6H), 1.37 (t, 4H), 3.77-3.87 (m, 6H, s at 3.80), 7.06 (d, 1H), 7.34 (s, 1H), 7.49 (m, 1H), 12.31 (s, 1H).

Example 28

4-[4-(tert-Butyl)piperidin-1-yl]-6-oxo-2-(3-thienylmethyl)-1,6-dihydropyrimidine-5-carbonitrile

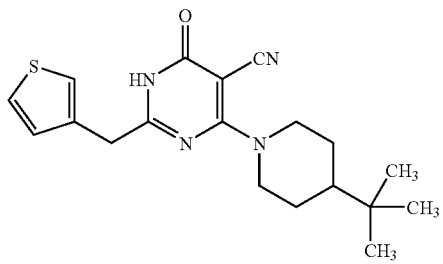

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 536 mg (3.80 mmol) of 4-tert-butylpiperidine to give 57 mg (42% of theory) of the title compound.

HPLC (method 12): R$_t$=4.9 min.
MS (ESIpos): m/z=357 [M+H]⁺
¹H-NMR (DMSO-d₆, 200 MHz): δ=0.82 (s, 9H), 1.02-1.42 (m, 3H), 1.74 (d, 2H), 2.96 (t, 2H), 3.78 (s, 2H), 4.72 (d, 2H), 7.06 (d, 1H), 7.33 (s, 1H), 7.49 (m, 1H), 12.35 (s, 1H).

Example 29

4-(4-Hydroxypiperidin-1-yl)-6-oxo-2-(3-thienylmethyl)-1,6-dihydropyrimidine-5-carbonitrile

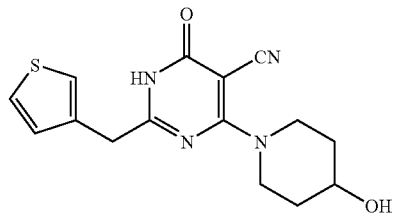

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 384 mg (3.80 mmol) of piperidin-4-ol to give 47 mg (39% of theory) of the title compound.

HPLC (method 12): R$_t$=3.50 min.
MS (ESIpos): m/z=317 [M+H]⁺
¹H-NMR (DMSO-d₆, 200 MHz): δ=1.29-1.50 (m, 2H), 1.72-1.90 (m, 2H), 3.42-3.60 (m, 2H), 3.68-3.86 (m, 3H, s at 3.79), 4.10-4.26 (m, 2H), 4.83 (d, 1H, OH), 7.07 (d, 1H), 7.35 (s, 1H), 7.50 (m, 1H), 11.79-12.29 (s, 1H, NH).

Example 30

4-[4-(2-Hydroxyethyl)piperidin-1-yl]-6-oxo-2-(3-thienylmethyl)-1,6-dihydropyrimidine-5-carbonitrile

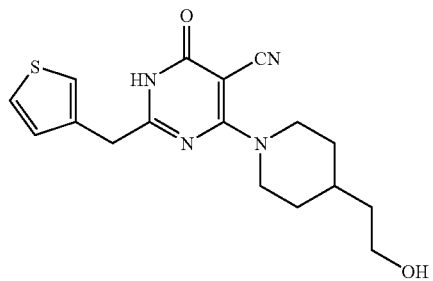

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 491 mg (3.80 mmol) of 2-(4-piperidinyl)ethan-1-ol to give 64 mg (49% of theory) of the title compound.

HPLC (method 12): $R_t$=3.70 min.

MS (ESIpos): m/z=345 [M+H]$^+$ $^1$H-NMR (DMSO-d$_6$, 300 MHz): δ=1.02-1.20 (m, 2H), 1.32-1.42 (q, 2H), 1.68-1.81 (m, 3H), 3.05 (t, 2H), 3.44 (q, 2H), 3.80 (s, 2H), 4.34 (t, 1H, OH), 4.62 (d, 2H), 7.06 (d, 1H), 7.34 (s, 1H), 7.49 (m, 1H), 12.31 (s, 1H, NH).

Example 31

4-[(2-Methoxyethyl)amino]-6-oxo-2-(3-thienylmethyl)-1,6-dihydropyrimidine-5-carbonitrile

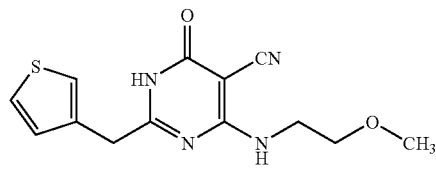

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 285 mg (3.80 mmol) of 2-methoxyethylamine to give 76 mg (69% of theory) of the title compound.

HPLC (method 12): $R_t$=3.7 min.

MS (ESIpos): m/z=291 [M+H]$^+$ $^1$H-NMR (DMSO-d$_6$, 300 MHz): δ=3.20 (s, 3H), 3.35-3.42 (m, 2H), 3.47-3.56 (m, 2H), 3.82 (s, 2H), 7.07 (d, 1H), 7.34 (s, 1H), 7.49 (m, 1H), 7.79 (s, 1H), 12.33 (s, 1H).

Example 32

4-(1,4-Dioxa-8-azaspiro[4.5]dec-8-yl)-6-oxo-2-(3-thienylmethyl)-1,6-dihydropyrimidine-5-carbonitrile

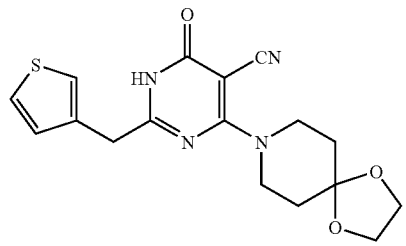

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 544 mg (3.80 mmol) of 1,4-dioxa-8-azaspiro[4.5]decane to give 65 mg (48% of theory) of the title compound.

HPLC (method 12): $R_t$=4.0 min.

MS (ESIpos): m/z=359 [M+H]$^+$ $^1$H-NMR (DMSO-d$_6$, 300 MHz): δ=1.70 (t, 4H), 3.81 (s, 2H), 3.86-3.95 (m, 8H, s at 3.92), 7.07 (d, 1H), 7.34 (s, 1H), 7.49 (m, 1H), 12.41 (s, 1H).

Example 33

4-(7,11-Dioxa-3-azaspiro[5.5]undec-3-yl)-6-oxo-2-(3-thienylmethyl)-1,6-dihydropyrimidine-5-carbonitrile

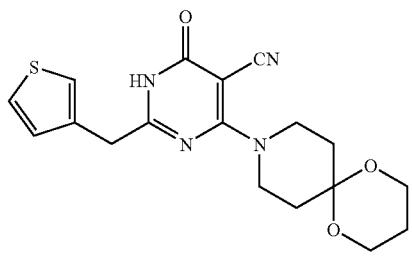

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 597 mg (3.80 mmol) of 1,5-dioxa-9-azaspiro[5.5]undecane to give 86 mg (61% of theory) of the title compound.

HPLC (method 12): $R_t$=4.0 min.

MS (ESIpos): m/z=373 [M+H]$^+$ $^1$H-NMR (DMSO-d$_6$, 200 MHz): δ=1.56 (m, 2H), 1.82-1.94 (m, 4H), 3.75-3.92 (m, 10H, s at 3.80), 7.07 (d, 1H), 7.35 (s, 1H), 7.50 (m, 1H), 12.43 (br. s, 1H).

Example 34

4-(4-Methylpiperazin-1-yl)-6-oxo-2-(3-thienylmethyl)-1,6-dihydropyrimidine-5-carbonitrile

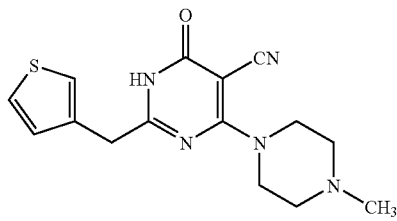

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 380 mg (3.80 mmol) of N-methylpiperazine to give 36 mg (30% of theory) of the title compound.

HPLC (method 12): $R_t$=3.2 min.

MS (ESIpos): m/z=316 [M+H]$^+$

¹H-NMR (DMSO-d₆, 200 MHz): δ=2.19 (s, 3H), 2.37 (t, 4H), 3.77-3.91 (m, 6H, s at 3.80), 7.07 (d, 1H), 7.35 (s, 1H), 7.50 (m, 1H), 12.43 (s, 1H).

Example 35

6-Oxo-4-(piperazin-1-yl)-2-(3-thienylmethyl)-1,6-dihydropyrimidine-5-carbonitrile

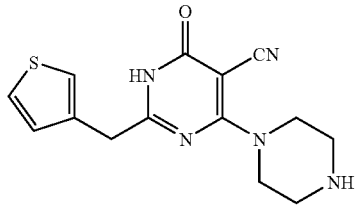

In analogy to the preparation of Example 1, 80 mg (0.30 mmol) of 4-(methylsulphanyl)-6-oxo-2-(3-thienylmethyl)-1,6-dihydropyrimidine-5-carbonitrile are reacted with 326 mg (3.80 mmol) of piperazine to give 45 mg (49% of theory) of the title compound.

HPLC (method 12): $R_t$=3.15 min.

MS (ESIpos): m/z=302 [M+H]⁺

¹H-NMR (DMSO-d₆, 200 MHz): δ=2.75 (t, 4H), 3.76-3.82 (m, 6H, s at 3.80), 7.06 (d, 1H), 7.34 (s, 1H), 7.49 (m, 1H).

Example 36

4-(Benzylamino)-6-oxo-2-(3-thienylmethyl)-1,6-dihydropyrimidine-5-carbonitrile

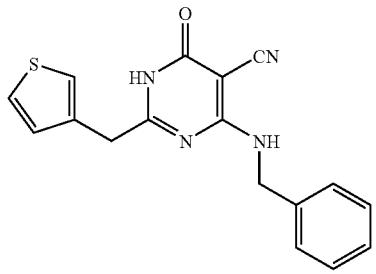

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 407 mg (3.80 mmol) of benzylamine to give 43 mg (35% of theory) of the title compound.

HPLC (method 12): $R_t$=4.3 min.

MS (ESIpos): m/z=323 [M+H]⁺

¹H-NMR (DMSO-d₆, 200 MHz): δ=3.80 (s, 2H), 4.52 (d, 2H), 6.95 (d, 1H), 7.16-7.32 (m, 6H), 7.45 (m, 1H), 8.49 (t, 1H), 12.40 (s, 1H).

Example 37

4-[(2-Methoxybenzyl)amino]-6-oxo-2-(3-thienylmethyl)-1,6-dihydropyrimidine-5-carbonitrile

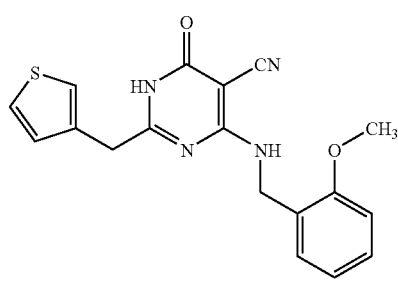

In analogy to the preparation of Example 1, 100 mg (0.38 mmol) of 4-(methylsulphanyl)-6-oxo-2-(3-thienylmethyl)-1,6-dihydropyrimidine-5-carbonitrile are reacted with 521 mg (3.80 mmol) of 2-methoxybenzylamine to give 62 mg (46% of theory) of the title compound.

HPLC (method 12): $R_t$=4.4 min.

MS (ESIpos): m/z=353 [M+H]⁺

¹H-NMR (DMSO-d₆, 300 MHz): δ=3.75 (s, 2H), 3.80 (s, 3H), 4.56 (d, 2H), 6.84-6.90 (m, 2H), 6.96-7.04 (m, 2H), 7.16 (s, 1H), 7.23 (t, 1H), 7.39 (m, 1H), 8.15 (t, 1H), 12.34 (s, 1H).

Example 38

4-[4-(2-Hydroxyethyl)piperidin-1-yl]-2-[2-(6-methoxypyridin-3-yl)benzyl]-6-oxo-1,6-dihydropyrimidine-5-carbonitrile

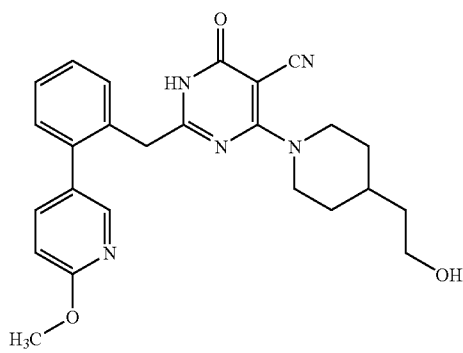

In analogy to the preparation of Example 1, 80 mg (0.22 mmol) of 2-[2-(6-methoxypyridin-3-yl)-benzyl]-4-(methylsulphanyl)-6-oxo-1,6-dihydropyrimidine-5-carbonitrile are reacted with 85 mg (0.65 mmol) of 2-(4-piperidinyl)ethan-1-ol to give 62 mg (63% of theory) of the title compound.

The following compound is prepared by the general synthetic route depicted in scheme II:

Scheme II:

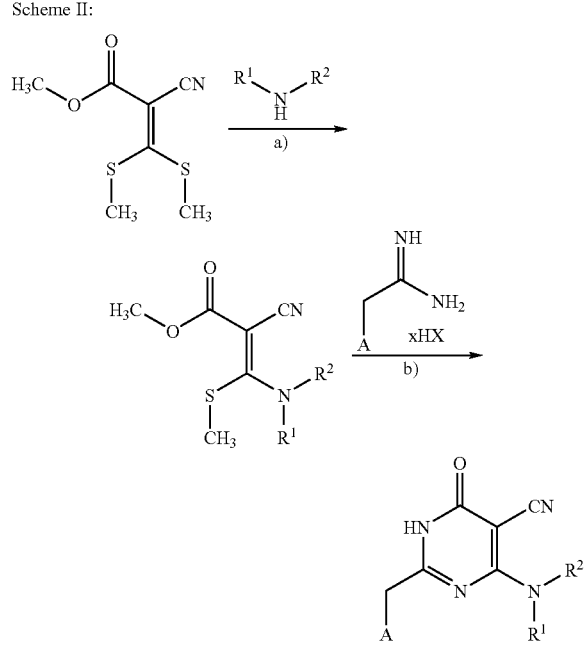

X = Cl, Br a) 1. toluene, boron trifluoride-etherate, RT, 30 min.; 2. amine component R¹R²NH, 150° C., 16 h; or: melt of the starting compounds at 150° C., 1-16 h; b) DMF, triethylamine, 100° C., 16 h or DMF, potassium carbonate, 90° C., 16 h.

Example 39

4-(Cyclohexylamino)-6-oxo-2-(3-thienylmethyl)-1,6-dihydropyrimidine-5-carbonitrile

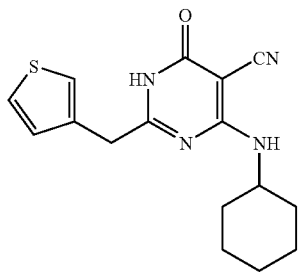

69.5 mg (0.39 mmol) of 2-(3-thienyl)ethanamidine hydrochloride are dissolved together with 100 mg (0.39 mmol) of methyl (2E/Z)-2-cyano-3-(cyclohexylamino)-3-methylthioprop-2-enoate and 159 mg (1.57 mmol) of triethylamine in 0.5 ml of DMF and stirred at 100° C. overnight. The cooled mixture is taken up in a little water and extracted with dichloromethane. The dichloromethane phase is dried over sodium sulphate and concentrated, and the residue is flash-chromatographed on silica gel (mobile phase: dichloromethane, then dichloromethane/methanol 200:1, 100:1). 23 mg (19% of theory) of the product are obtained.

HPLC (method 12): $R_t$=4.55 min.

MS (DCI, NH₃): m/z=315 [M+H]⁺

¹H-NMR (DMSO-d₆, 400 MHz): δ=0.98-1.43 (m, 5H), 1.53-1.74 (m, 5H), 3.78-3.94 (m, 3H, s at 3.82), 7.06 (d, 1H), 7.33 (s, 1H), 7.50 (m, 1H), 7.54 (m, 1H), 12.28 (s, 1H).

Example 40

4-(4-Formylpiperazin-1-yl)-6-oxo-2-(3-thienylmethyl)-1,6-dihydropyrimidine-5-carbonitrile

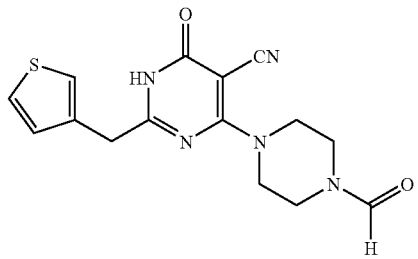

11.3 mg (0.17 mmol) of imidazole are introduced together with 33.6 mg (0.33 mmol) of triethylamine and 7.64 mg (0.17 mmol) of formic acid into 5 ml of dichloromethane under an argon atmosphere and cooled to 0° C. Then a solution of 21.1 mg (0.17 mmol) of oxalyl chloride in dichloromethane is added dropwise, and the mixture is then stirred for 15 min. 50 mg (0.17 mmol) of 6-oxo-4-(piperazin-1-yl)-2-(3-thienylmethyl)-1,6-dihydropyrimidine-5-carbonitrile are added, and the mixture is stirred at RT overnight. It is then washed with 1 N potassium bisulphate solution, the dichloromethane phase is dried over sodium sulphate and concentrated, and the residue is flash-chromatographed on silica gel (mobile phase: dichloromethane/methanol 100:1, 80:1, 60:1). 16 mg (29% of theory) of the title compound are obtained.

HPLC (method 12): $R_t$=3.4 min.

MS (ESIpos): m/z=330 [M+H]⁺

¹H-NMR (DMSO-d₆, 200 MHz): δ=3.42-3.54 (m, 4H), 3.79-3.94 (m, 6H, s at 3.82), 7.09 (d, 1H), 7.36 (s, 1H), 7.51 (m, 1H), 8.06 (s, 1H), 12.55 (s, 1H).

Example 41

4-(4-Acetylpiperazin-1-yl)-6-oxo-2-(3-thienylmethyl)-1,6-dihydropyrimidine-5-carbonitrile

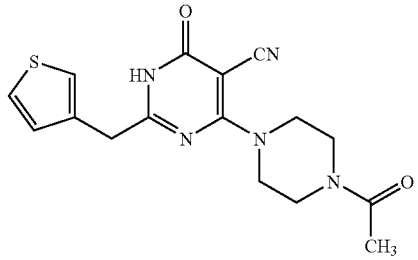

50 mg (0.17 mmol) of 6-oxo-4-(piperazin-1-yl)-2-(3-thienylmethyl)-1,6-dihydropyrimidine-5-carbonitrile are dissolved together with 34 mg (0.33 mmol) of triethylamine in DMF and stirred with 14.3 mg (0.18 mmol) of acetyl chloride at RT overnight. The mixture is then diluted with dichloromethane and washed with water. The organic phase is separated off and dried over sodium sulphate and the residue is flash-chromatographed on silica gel (mobile phase: dichloromethane/methanol 100:1, 80:1, 60:1). 42 mg (74% of theory) of the title compound are obtained.

HPLC (method 12): $R_t$=3.5 min.

MS (ESIpos): m/z=344 [M+H]$^+$ $^1$H-NMR (DMSO-d$_6$, 300 MHz): δ=2.02 (s, 3H), 3.50-3.61 (m, 4H), 3.80-3.95 (m, 6H, s at 3.82), 7.08 (d, 1H), 7.36 (s, 1H), 7.50 (m, 1H), 12.47 (s, 1H).

Example 42

4-(4-Ethylpiperazin-1-yl)-6-oxo-2-(3-thienylmethyl)-1,6-dihydropyrimidine-5-carbonitrile

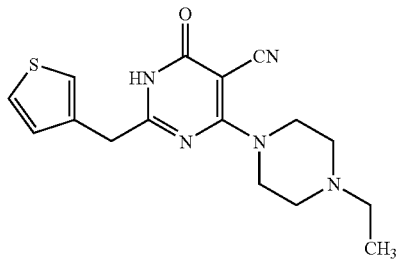

50 mg (0.17 mmol) of 6-oxo-4-(piperazin-1-yl)-2-(3-thienylmethyl)-1,6-dihydropyrimidine-5-carbonitrile are dissolved together with 34 mg (0.33 mmol) of triethylamine in DMF and, after addition of 19.9 mg (0.18 mmol) of bromoethane, stirred at RT overnight. The mixture is then diluted with dichloromethane and washed with water. The organic phase is separated off and dried over sodium sulphate, and the residue is flash-chromatographed on silica gel (mobile phase: dichloromethane/methanol 100:1, 80:1, 60:1, 40:1). 38 mg (70% of theory) of the title compound are obtained.

HPLC (method 12): $R_t$=3.3 min.

MS (ESIpos): m/z=330 [M+H]$^+$ $^1$H-NMR (DMSO-d$_6$, 300 MHz): δ=1.00 (t, 3H), 2.34 (q, 2H), 2.42 (t, 4H), 3.80 (s, 2H), 3.86 (t, 4H), 7.06 (d, 1H), 7.34 (s, 1H), 7.49 (m, 1H), 12.39 (s, 1H).

The exemplary embodiments listed in the following table are prepared in analogy to the examples described above:

| Example No. | Structure | LC-MS: m/z [M + H]$^+$ | $R_t$ [min] | HPLC/LC-MS method |
|---|---|---|---|---|
| 43 | 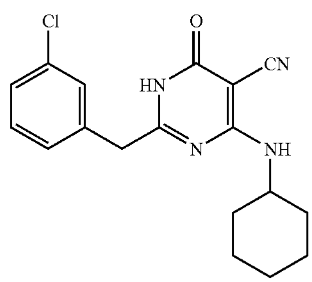 | 344 | 4.8 | 12 |
| 44 | 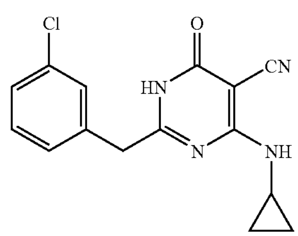 | 302 | 4.2 | 12 |
| 45 | 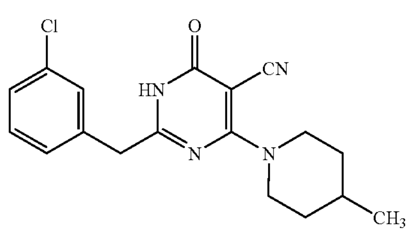 | 344 | 4.8 | 12 |

-continued

| Example No. | Structure | LC-MS: m/z [M + H]+ | R_t [min] | HPLC/LC-MS method |
|---|---|---|---|---|
| 46 | 3-chlorobenzyl-pyrimidinone-CN-piperidine | 330 | 4.6 | 12 |
| 47 | 3-fluorobenzyl-pyrimidinone-CN-pyrrolidine | 299 | 1.99 | 10 |
| 48 | 3-fluorobenzyl-pyrimidinone-CN-(4-(2-hydroxyethyl)piperidine) | 357 | 1.83 | 6 |
| 49 | 3-fluorobenzyl-pyrimidinone-CN-(1,4-dioxa-8-azaspiro[4.5]decane) | 371 | 3.17 | 7 |
| 50 | 3-fluorobenzyl-pyrimidinone-CN-(4-hydroxypiperidine) | 329 | 1.45 | 5 |
| 51 | 3-methylbenzyl-pyrimidinone-CN-(4,4-dimethylpiperidine) | 337 | 3.19 | 2 |

-continued

| Example No. | Structure | LC-MS: m/z [M + H]+ | R<sub>t</sub> [min] | HPLC/LC-MS method |
|---|---|---|---|---|
| 52 | 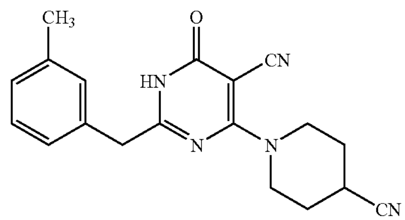 | 334 | 2.54 | 7 |
| 53 | 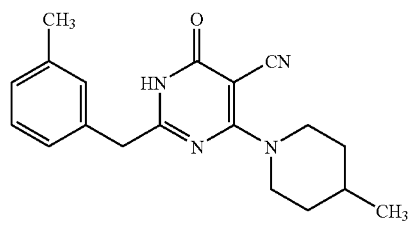 | 323 | 2.36 | 10 |
| 54 | 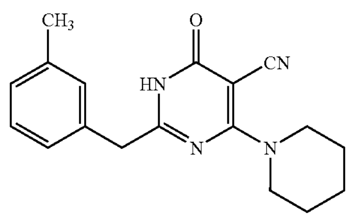 | 309 | 2.87 | 7 |
| 55 | 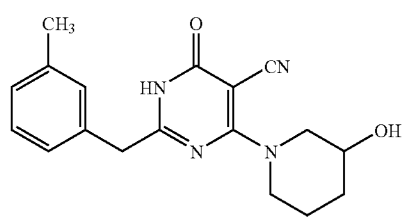 | 325 | 2.38 | 2 |
| 56 | 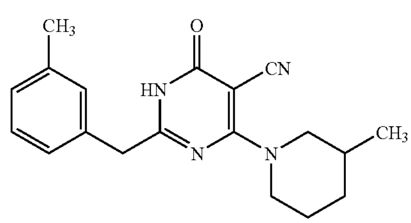 | 323 | 3.06 | 2 |
| 57 | 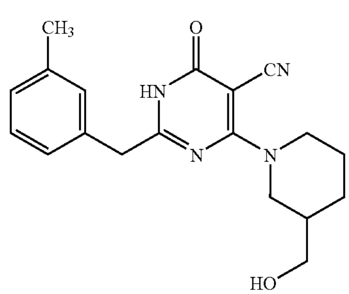 | 339 | 2.99 | 7 |

-continued

| Example No. | Structure | LC-MS: m/z [M + H]+ | $R_t$ [min] | HPLC/LC-MS method |
|---|---|---|---|---|
| 58 | 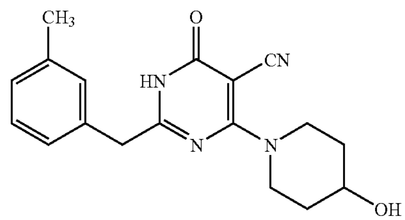 | 325 | 1.74 | 10 |
| 59 | 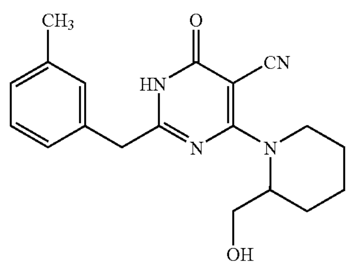 | 339 | 1.79 | 5 |
| 60 | 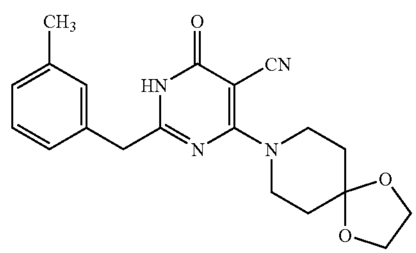 | 367 | 2.7 | 2 |
| 61 | 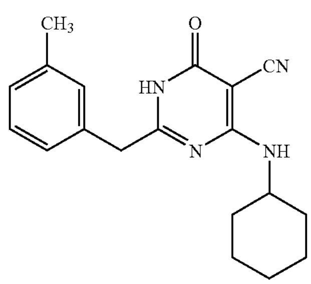 | 323 | 3.1 | 7 |
| 62 | 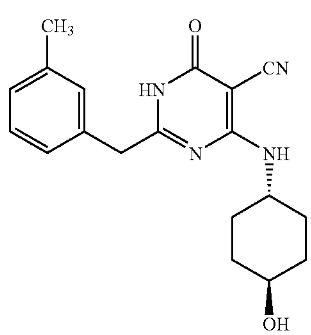 | 339 | 2.19 | 7 |

-continued

| Example No. | Structure | LC-MS: m/z [M + H]⁺ | $R_t$ [min] | HPLC/LC-MS method |
|---|---|---|---|---|
| 63 | 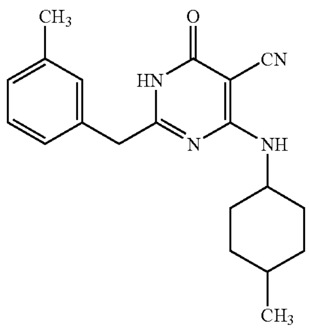 | 337 | 3.3 | 7 |
| 64 | 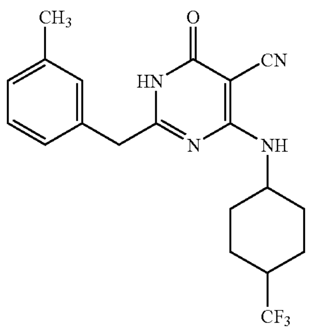 | 391 | 2.6 | 4 |
| 65 | 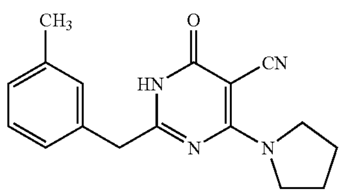 | 295 | 2.75 | 2 |
| 66 | 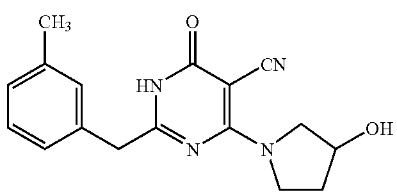 | 311 | 1.73 | 10 |
| 67 | 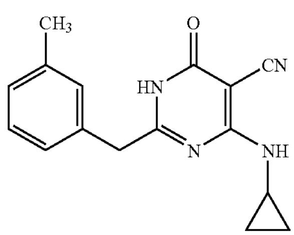 | 281 | 3.18 | 7 |
| 68 | 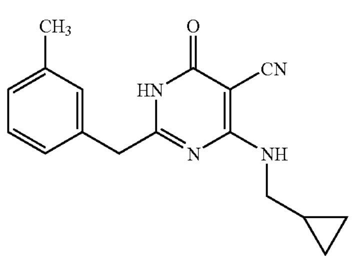 | 295 | 2.73 | 7 |

-continued

| Example No. | Structure | LC-MS: m/z [M + H]+ | R_t [min] | HPLC/LC-MS method |
|---|---|---|---|---|
| 69 | 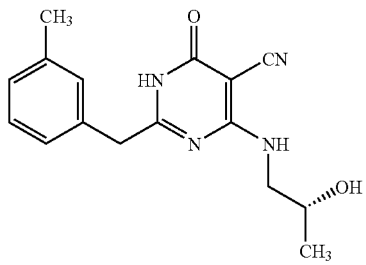 | 299 | 2.22 | 7 |
| 70 | 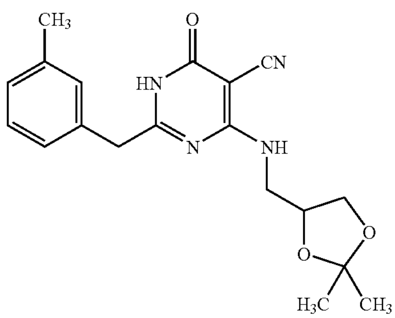 | 355 | 2.63 | 2 |
| 71 | 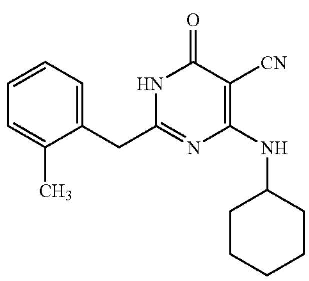 | 323 | 2.37 | 10 |
| 72 | 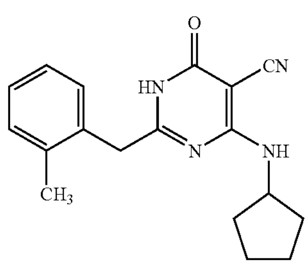 | 309 | 2.27 | 10 |
| 73 | 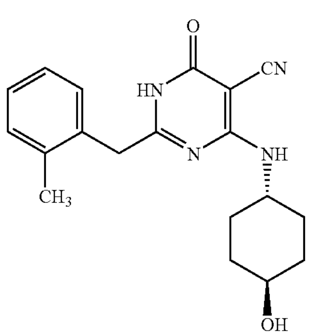 | 339 | 2.19 | 2 |

-continued
| Example No. | Structure | LC-MS: m/z [M + H]+ | R_t [min] | HPLC/LC-MS method |
|---|---|---|---|---|
| 74 | 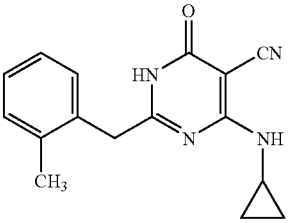 | 281 | 2.02 | 6 |
| 75 | 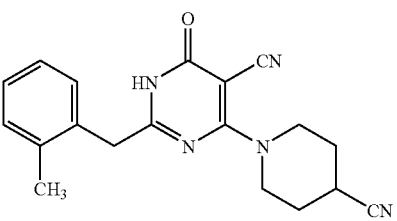 | 334 | 2.47 | 7 |
| 76 | 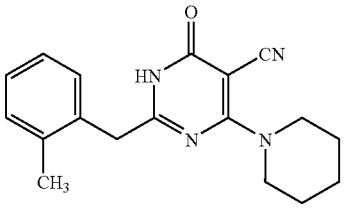 | 309 | 2.19 | 10 |
| 77 | 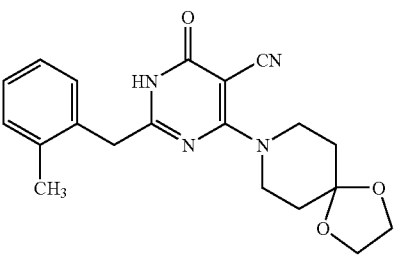 | 367 | 2.81 | 1 |
| 78 | 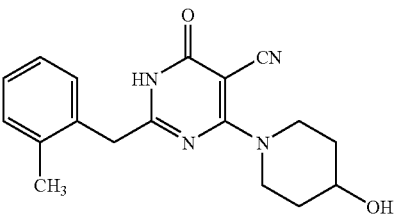 | 325 | 2.35 | 2 |
| 79 | 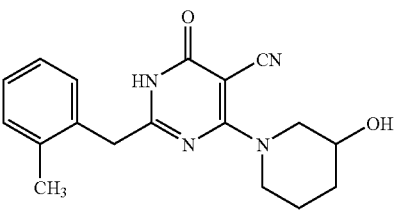 | 325 | 2.35 | 2 |

-continued

| Example No. | Structure | LC-MS: m/z [M + H]+ | R_t [min] | HPLC/LC-MS method |
|---|---|---|---|---|
| 80 | 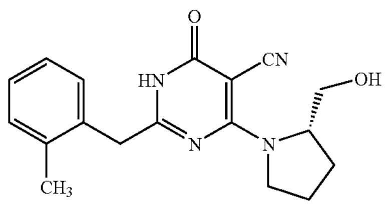 | 325 | 1.76 | 4 |
| 81 | 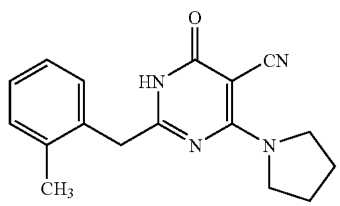 | 295 | 3.24 | 7 |
| 82 | 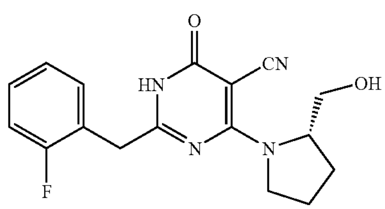 | 329 | 1.69 | 10 |
| 83 | 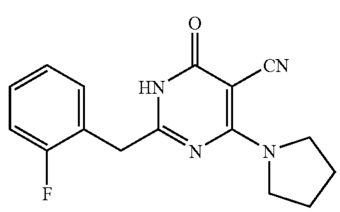 | 299 | 3.19 | 7 |
| 84 | 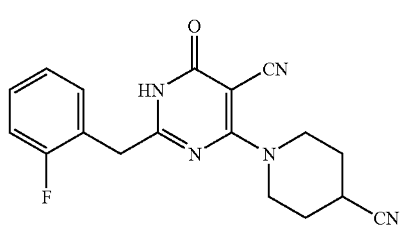 | 338 | 1.88 | 10 |
| 85 | 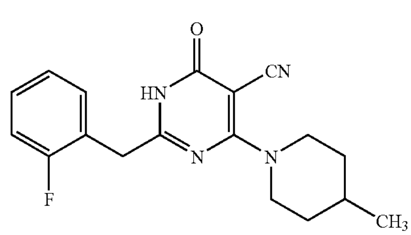 | 327 | 3.5 | 2 |

-continued

| Example No. | Structure | LC-MS: m/z [M + H]+ | R_t [min] | HPLC/LC-MS method |
|---|---|---|---|---|
| 86 | 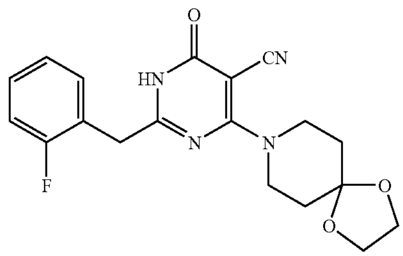 | 371 | 1.95 | 10 |
| 87 | 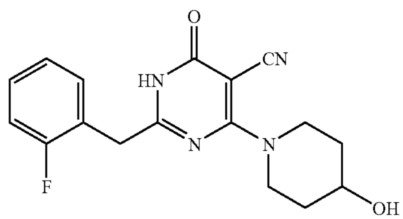 | 329 | 1.63 | 10 |
| 88 | 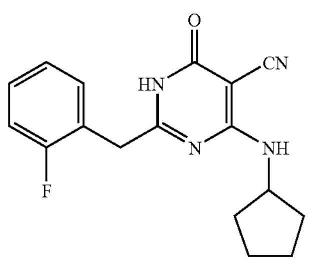 | 313 | 3.4 | 2 |
| 89 | 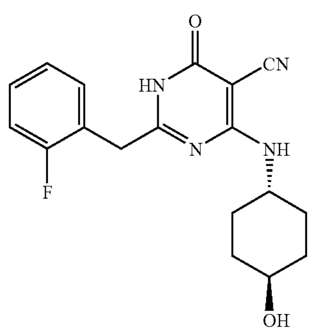 | 343 | 2.71 | 7 |
| 90 | 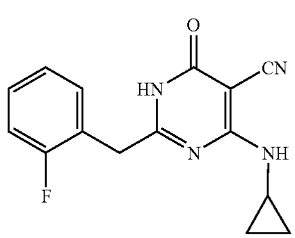 | 285 | 1.84 | 10 |

-continued

| Example No. | Structure | LC-MS: m/z [M + H]+ | R_t [min] | HPLC/LC-MS method |
|---|---|---|---|---|
| 91 | 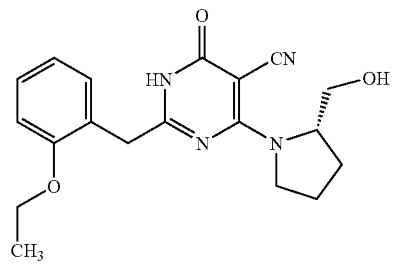 | 355 | 1.97 | 6 |
| 92 | 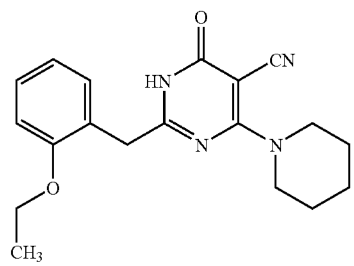 | 339 | 2.19 | 6 |
| 93 | 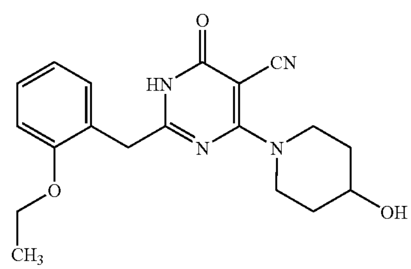 | 255 | 1.61 | 6 |
| 94 | 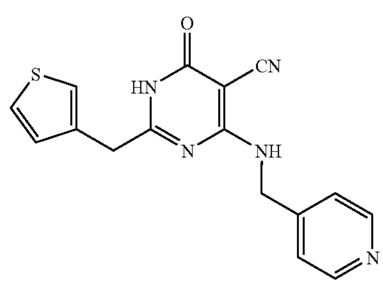 | 324 | 3.2 | 12 |
| 95 | 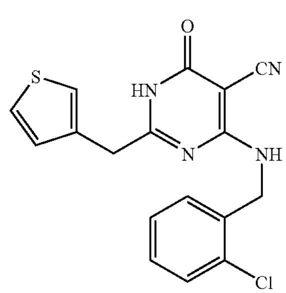 | 358 | 4.5 | 12 |

-continued

| Example No. | Structure | LC-MS: m/z [M + H]+ | R_t [min] | HPLC/LC-MS method |
|---|---|---|---|---|
| 96 | 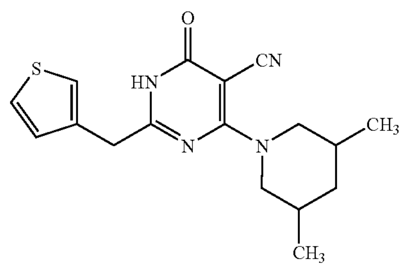 | 329 | 4.7 | 12 |
| 97 | 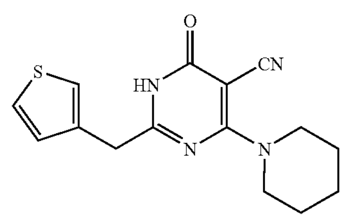 | 301 | 4.3 | 12 |
| 98 | 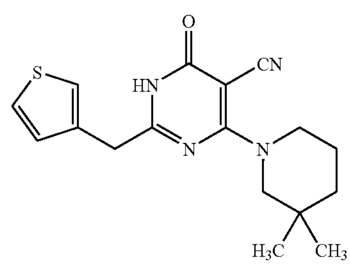 | 329 | 4.6 | 12 |
| 99 | 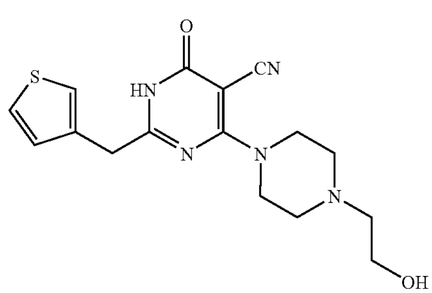 | 346 | 3.2 | 12 |
| 100 | 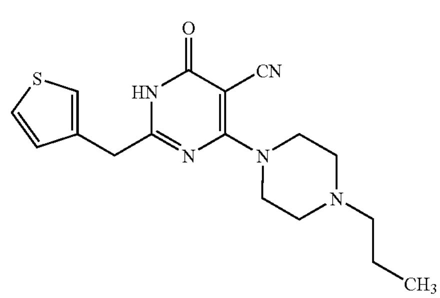 | 344 | 3.4 | 12 |

-continued

| Example No. | Structure | LC-MS: m/z [M + H]+ | R_t [min] | HPLC/LC-MS method |
|---|---|---|---|---|
| 101 | 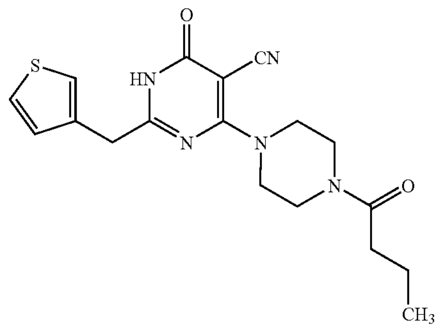 | 372 | 3.9 | 12 |
| 102 | 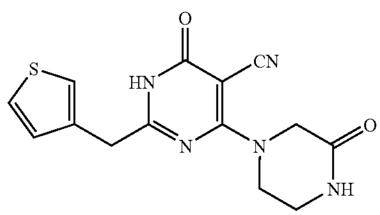 | 316 | 4.3 | 13 |
| 103 | 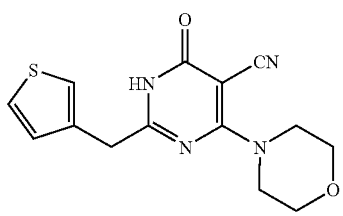 | 303 | 3.8 | 12 |
| 104 | 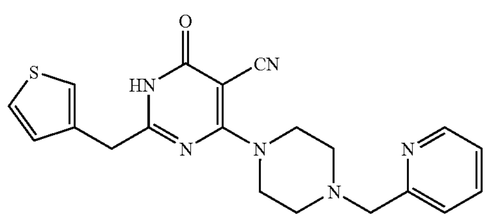 | 393 | 3.5 | 12 |
| 105 | 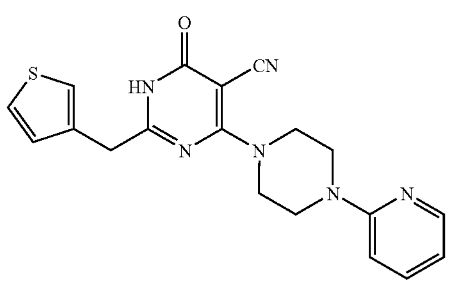 | 379 | 3.5 | 12 |
| 106 | 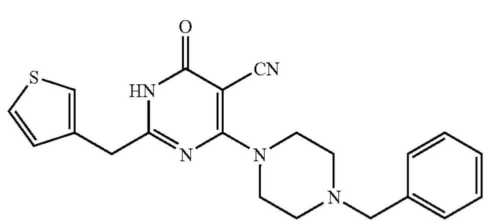 | 392 | 3.8 | 12 |

-continued

| Example No. | Structure | LC-MS: m/z [M + H]+ | R_t [min] | HPLC/LC-MS method |
|---|---|---|---|---|
| 107 | 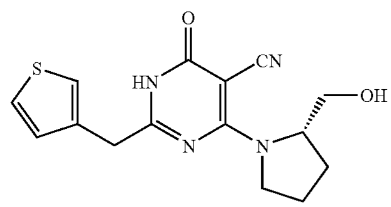 | 317 | 1.46 | 5 |
| 108 | 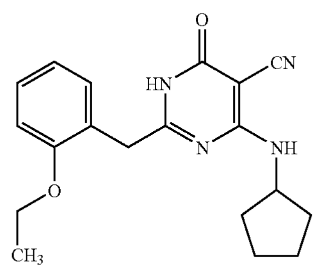 | 339 | 2.42 | 6 |
| 109 | 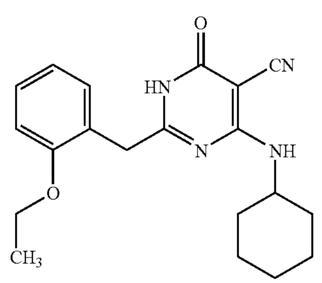 | 353 | 2.54 | 6 |
| 110 | 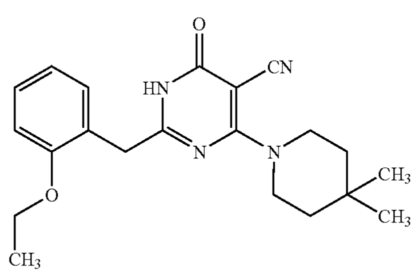 | 367 | 2.63 | 6 |
| 111 | 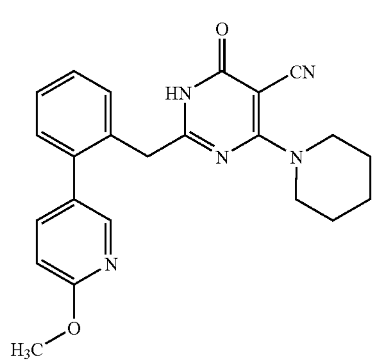 | 402 | 2.15 | 5 |

-continued

| Example No. | Structure | LC-MS: m/z [M + H]+ | R$_t$ [min] | HPLC/LC-MS method |
|---|---|---|---|---|
| 112 | 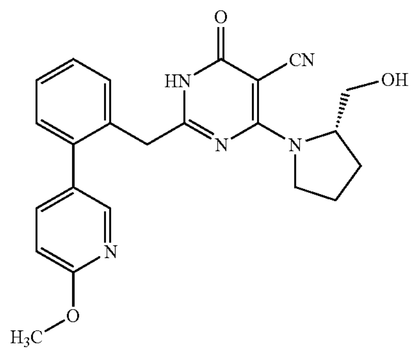 | 418 | 1.92 | 6 |
| 113 | 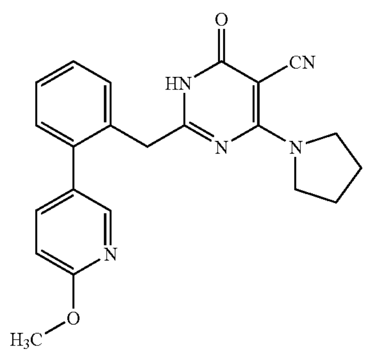 | 388 | 2.02 | 5 |
| 114 | 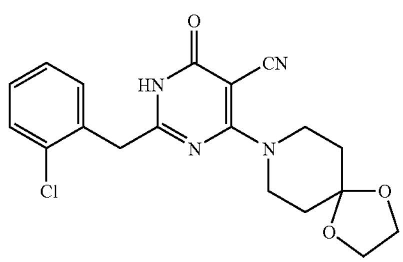 | 387 | 1.9 | 5 |
| 115 | 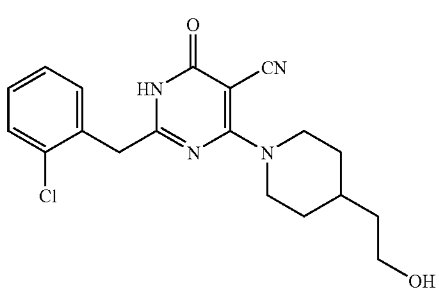 | 373 | 1.94 | 6 |
| 116 | 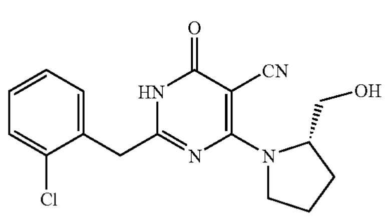 | 345 | 1.84 | 6 |

-continued

| Example No. | Structure | LC-MS: m/z [M + H]+ | R$_t$ [min] | HPLC/LC-MS method |
| --- | --- | --- | --- | --- |
| 117 | 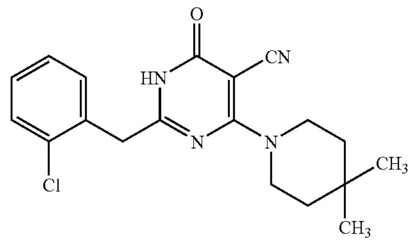 | 357 | 2.61 | 6 |
| 118 | 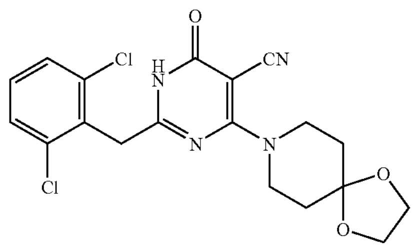 | 421 | 1.99 | 5 |
| 119 | 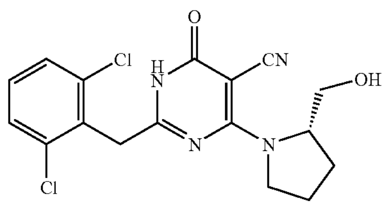 | 379 | 1.89 | 6 |
| 120 | 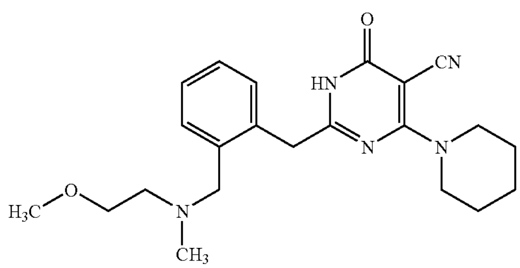 | 396 | 1.18 | 5 |
| 121 | 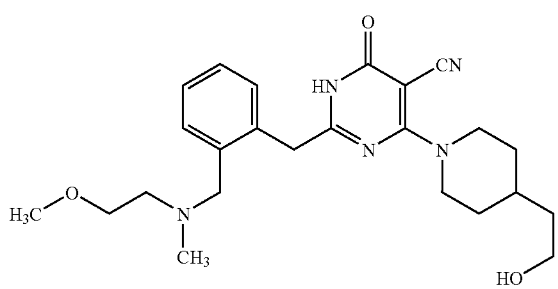 | 440 | 1.03 | 5 |
| 122 | 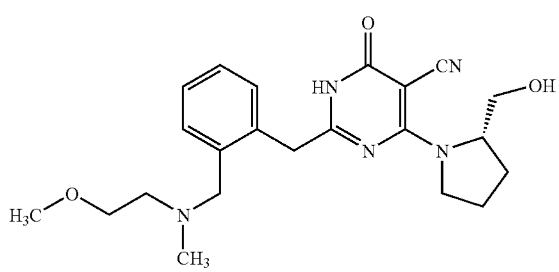 | 412 | 0.92 | 5 |

-continued

| Example No. | Structure | LC-MS: m/z [M + H]+ | R$_t$ [min] | HPLC/LC-MS method |
|---|---|---|---|---|
| 123 | 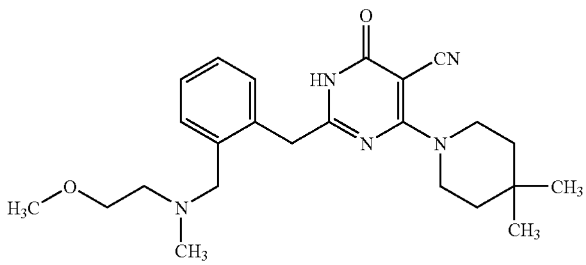 | 424 | 1.46 | 5 |
| 124 | 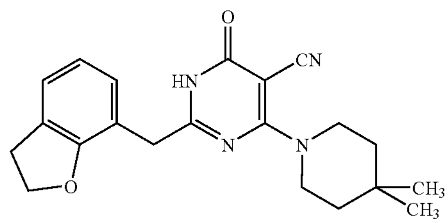 | 365 | 2.31 | 5 |
| 125 | 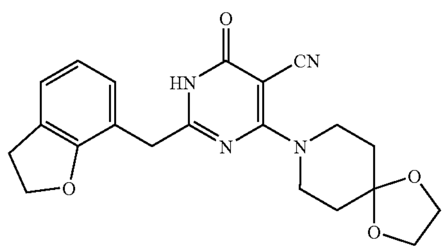 | 395 | 1.85 | 5 |
| 126 | 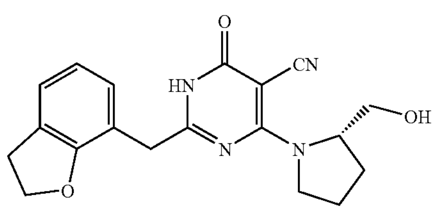 | 353 | 1.54 | 5 |
| 127 | 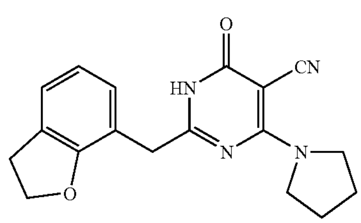 | 323 | 1.89 | 5 |
| 128 | 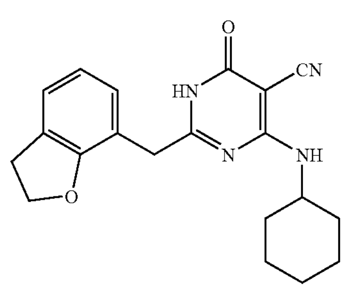 | 351 | 2.2 | 5 |

-continued

| Example No. | Structure | LC-MS: m/z [M + H]⁺ | R$_t$ [min] | HPLC/LC-MS method |
| --- | --- | --- | --- | --- |
| 129 | 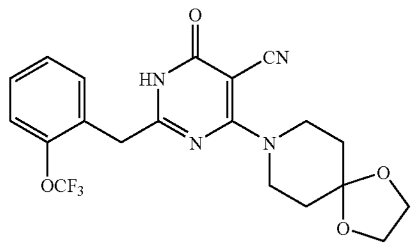 | 437 | 2.28 | 6 |
| 130 | 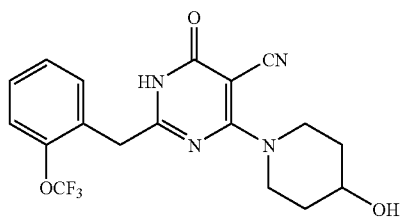 | 395 | 1.86 | 4 |
| 131 | 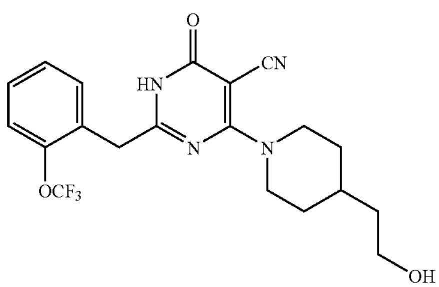 | 423 | 2.01 | 4 |
| 132 | 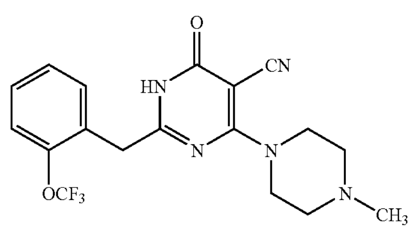 | 393 | 1.3 | 4 |
| 133 | 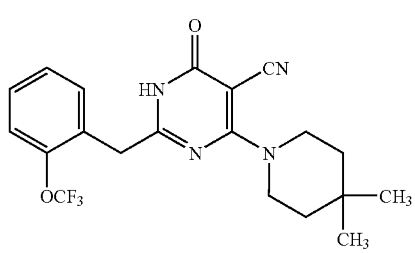 | 407 | 2.5 | 5 |
| 134 | 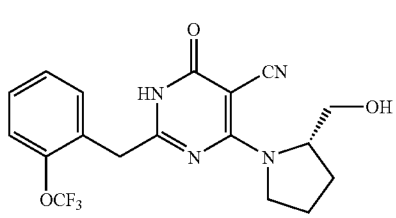 | 395 | 1.74 | 5 |

-continued

| Example No. | Structure | LC-MS: m/z [M + H]+ | R$_t$ [min] | HPLC/LC-MS method |
|---|---|---|---|---|
| 135 | 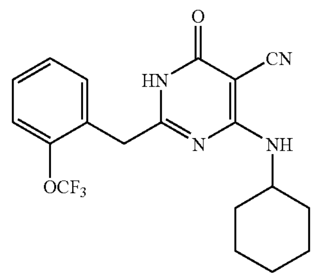 | 393 | 2.63 | 6 |
| 136 | 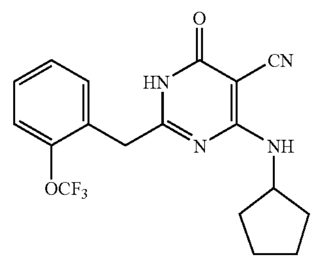 | 379 | 2.31 | 5 |
| 137 | 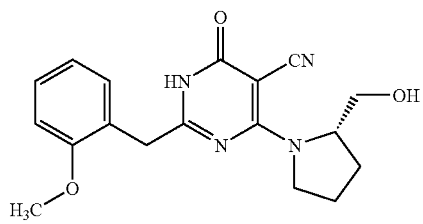 | 341 | 1.54 | 5 |
| 138 | 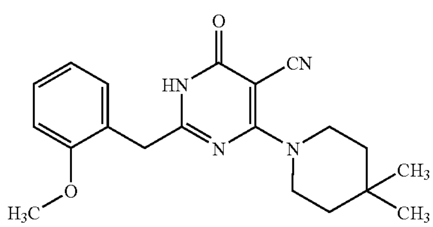 | 353 | 2.5 | 4 |
| 139 | 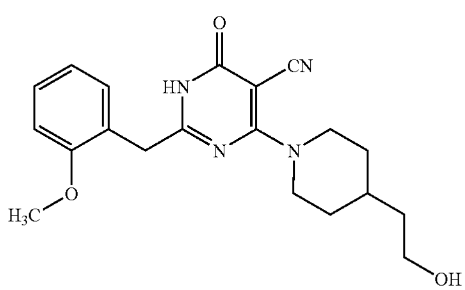 | 369 | 1.84 | 4 |
| 140 | 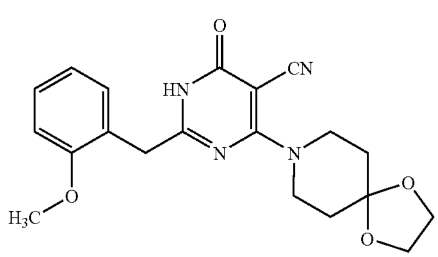 | 383 | 2.1 | 6 |

-continued

| Example No. | Structure | LC-MS: m/z [M + H]⁺ | R_t [min] | HPLC/LC-MS method |
|---|---|---|---|---|
| 141 | 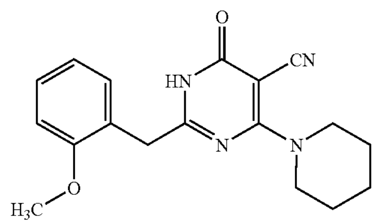 | 325 | 2.04 | 5 |
| 142 | 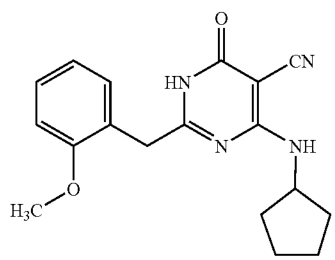 | 325 | 2.28 | 4 |
| 143 | 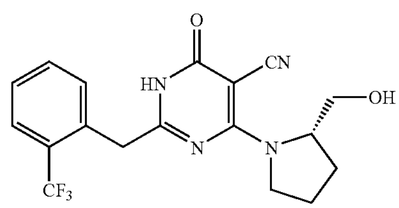 | 379 | 1.85 | 4 |
| 144 | 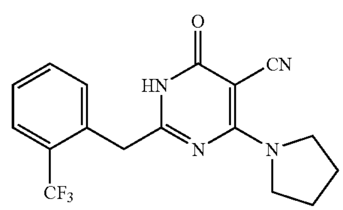 | 349 | 2.07 | 5 |
| 145 | 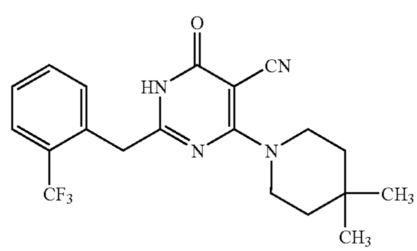 | 391 | 2.44 | 5 |
| 146 | 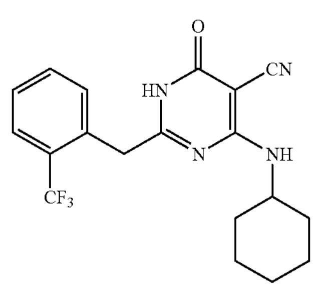 | 377 | 2.48 | 4 |

| Example No. | Structure | LC-MS: m/z [M + H]+ | R$_t$ [min] | HPLC/LC-MS method |
|---|---|---|---|---|
| 147 | 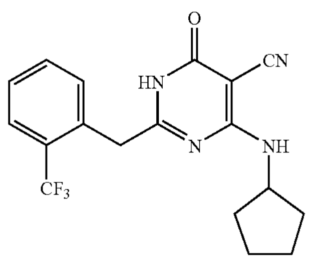 | 363 | 2.45 | 6 |
| 148 | 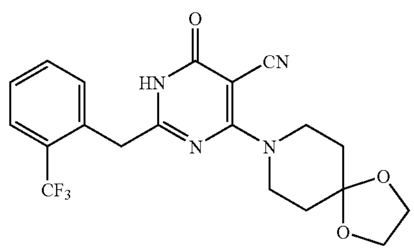 | 421 | 2.15 | 4 |
| 149 | 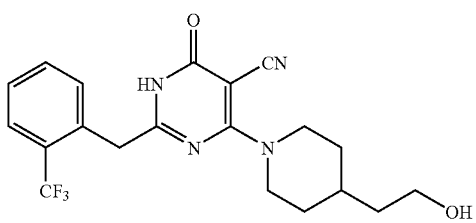 | 407 | 1.94 | 4 |
| 150 | 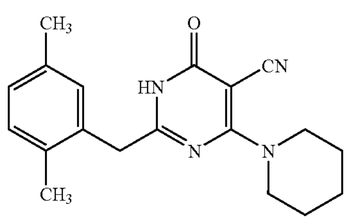 | 323 | 2.47 | 6 |
| 151 | 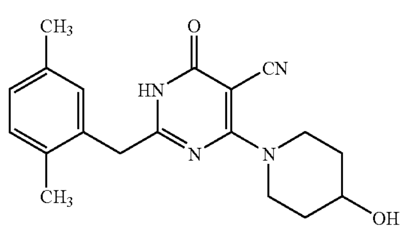 | 339 | 1.67 | 5 |
| 152 | 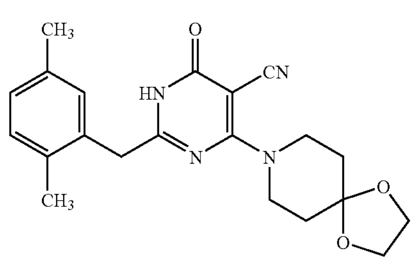 | 381 | 2.07 | 5 |

-continued

| Example No. | Structure | LC-MS: m/z [M + H]+ | R$_t$ [min] | HPLC/LC-MS method |
| --- | --- | --- | --- | --- |
| 153 | 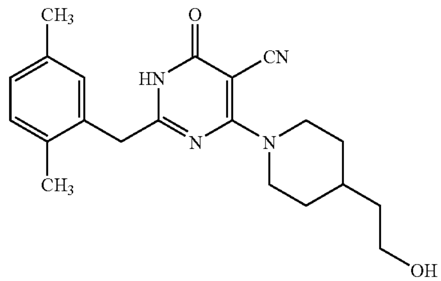 | 367 | 1.99 | 4 |
| 154 | 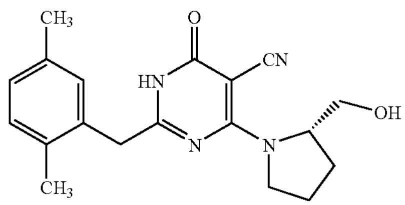 | 229 | 1.98 | 6 |
| 155 | 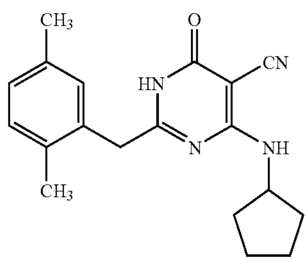 | 323 | 2.53 | 6 |
| 156 | 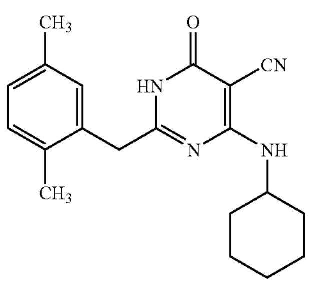 | 337 | 2.65 | 6 |
| 157 | 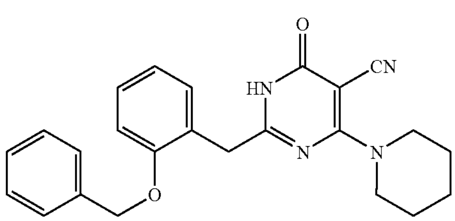 | 401 | 2.59 | 6 |
| 158 | 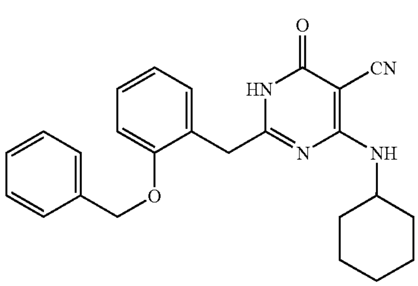 | 415 | 2.75 | 6 |

-continued

| Example No. | Structure | LC-MS: m/z [M + H]+ | R$_t$ [min] | HPLC/LC-MS method |
|---|---|---|---|---|
| 159 | 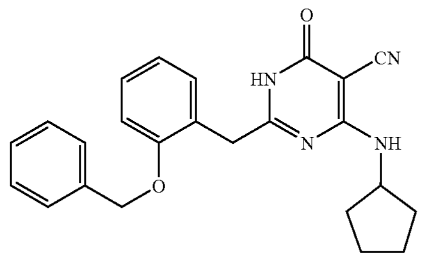 | 401 | 2.43 | 5 |
| 160 | 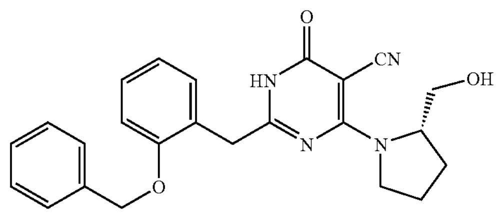 | 417 | 1.9 | 5 |
| 161 | 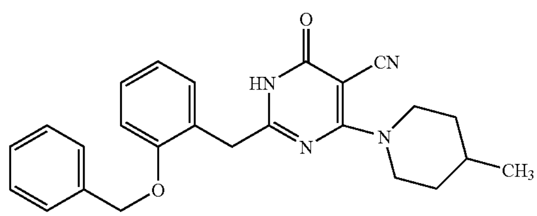 | 415 | 2.72 | 6 |
| 162 | 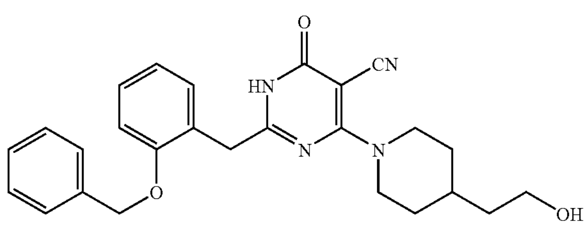 | 445 | 1.97 | 5 |
| 163 | 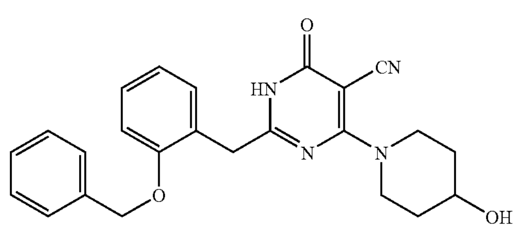 | 417 | 1.82 | 5 |
| 164 | 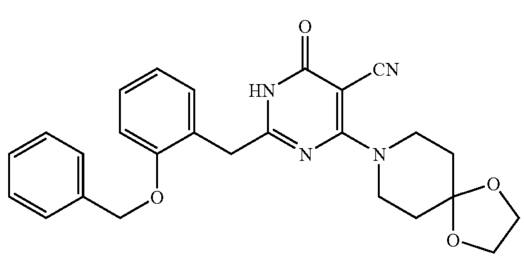 | 459 | 2.2 | 5 |

The invention claimed is:
1. A method for the treatment of a condition concerning impairment of learning and memory in a patient in need of such treatment, comprising administering a therapeutically amount of a compound of formula (I) to said patient,

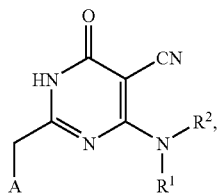
(I)

in which
A is phenyl; heteroaryl which is an aromatic, monocyclic radical having 5 to 6 ring atoms and 1 to 3 heteroatoms selected from S, O and N; or a group of the formula

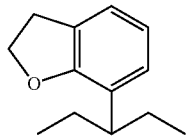

where phenyl and heteroaryl are optionally substituted by up to 2 radicals independently of one another selected from the group of heteroaryl which is being an aromatic, monocyclic radical having 5 to 6 ring atoms and 1 to 3 heteroatoms selected from S, O and N; halogen; $C_1$-$C_6$-alkyl; $C_1$-$C_6$-alkoxy; trifluoromethyl; trifluoromethoxy; benzyloxy and benzyl;
where $C_1$-$C_6$-alkyl is optionally substituted by a group of the formula —$NR^3R^4$ in which $R^3$ is $C_1$-$C_6$-alkyl and $R^4$ is hydrogen or $C_1$-$C_6$-alkoxy($C_1$-$C_6$)alkyl, and
heteroaryl is optionally substituted by $C_1$-$C_6$-alkoxy, $R^1$ is $C_3$-$C_8$-cycloalkyl, $C_1$-$C_6$-alkyl, $C_1$-$C_6$-alkoxy($C_1$-$C_6$)alkyl, benzyl or a group of the formula

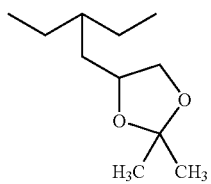

where $C_3$-$C_8$-cycloalkyl is optionally substituted by hydroxy, $C_1$-$C_6$-alkyl or trifluoromethyl,
$C_1$-$C_6$-alkyl is optionally substituted by heteroaryl, $C_3$-$C_8$-cycloalkyl or hydroxy,
and benzyl is optionally substituted by $C_1$-$C_6$-alkoxy or halogen,
$R^2$ is hydrogen,
or
$R^1$ and $R^2$ together with the nitrogen atom to which they are bonded form a 5- to 6-membered heterocyclyl group which is a monocyclic, saturated or partially unsaturated heterocyclic radical having 5 to 6 ring atoms and 1 to 2 heteroatoms selected from N, O, and S which is optionally substituted by up to 2 substituents independently of one another selected from $C_1$-$C_6$-alkyl; hydroxy; cyano; oxo; heteroaryl which is an aromatic, monocyclic radical having 5 to 6 ring atoms and 1 to 3 heteroatoms selected from S, O and N; benzyl; formyl; $C_1$-$C_6$-alkylcarbonyl; and the following groups

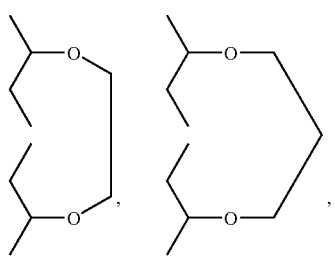

which are linked via the two oxygen atoms to one of the carbon atoms in the heterocycle,
where $C_1$-$C_6$-alkyl is optionally substituted by hydroxy or heteroaryl which is an aromatic, monocyclic radical having 5 to 6 ring atoms and up to 3 heteroatoms selected from S, O and N;
or a salt thereof.

2. A method according to claim 1, where in the compound of formula (I):
A is phenyl, heteroaryl which is an aromatic, monocyclic radical having 5 to 6 ring atoms and 1 to 3 heteroatoms selected from S, O and N;
or a group of the formula

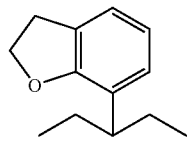

where phenyl and heteroaryl are optionally substituted by up to 2 radicals independently of one another selected from the group of heteroaryl which is an aromatic, monocyclic radical having 5 to 6 ring atoms and 1 to 3 heteroatoms selected from S, O and N; halogen; $C_1$-$C_4$-alkyl; $C_1$-$C_4$-alkoxy; trifluoromethyl; trifluoromethoxy; benzyloxy; and benzyl;
where $C_1$-$C_4$-alkyl is optionally substituted by a group of the formula —$NR^3R^4$ in which $R^3$ is $C_1$-$C_4$-alkyl and $R^4$ is hydrogen or $C_1$-$C_4$-alkoxy($C_1$-$C_4$)alkyl, and
heteroaryl is optionally substituted by $C_1$-$C_4$-alkoxy,
$R^1$ is $C_3$-$C_6$-cycloalkyl, $C_1$-$C_4$-alkyl, $C_1$-$C_4$-alkoxy($C_1$-$C_4$)alkyl, benzyl or a group of the formula

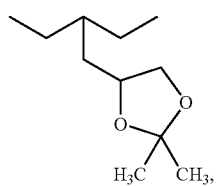

where $C_3$-$C_6$-cycloalkyl is optionally substituted by hydroxy, $C_1$-$C_4$-alkyl or trifluoromethyl, $C_1$-$C_4$-alkyl is optionally substituted by heteroaryl which is an aromatic, monocyclic radical having 5 to 6 ring atoms and 1 to 3 heteroatoms selected from S, O and N; $C_3$-$C_6$-cycloalkyl; or hydroxy, and benzyl is optionally substituted by $C_1$-$C_4$-alkoxy or halogen, $R^2$ is hydrogen, or $R^1$ and $R^2$ together with the nitrogen atom to which they are bonded form a 5- to 6-membered heterocyclyl which is a monocyclic, saturated or partially unsaturated heterocyclic radical having 5 to 6 ring atoms and 1 to 2 heteroatoms selected from N, O and S, which is optionally substituted by up to 2 substituents independently of one another selected from the group of $C_1$-$C_4$-alkyl, hydroxy, cyano, oxo, heteroaryl which is an aromatic, monocyclic radical having 5 to 6 ring atoms and 1 to 3 heteroatoms selected from S, O and N; benzyl; formyl; $C_1$-$C_4$-alkylcarbonyl; and the following groups

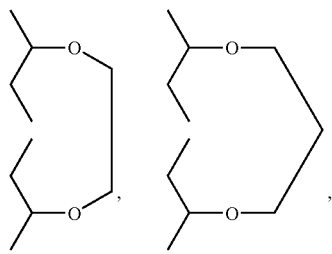

which are linked via the two oxygen atoms to one of the carbon atoms in the heterocycle, where $C_1$-$C_4$-alkyl is optionally substituted by hydroxy or heteroaryl which is an aromatic, monocyclic radical having 5 to 6 ring atoms and 1 to 3 heteroatoms selected from S, O and N, or a salt thereof.

3. A method according to claim 1, where in the compound of formula (I):

A is phenyl, thienyl or a group of the formula

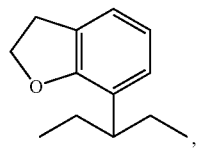

where phenyl and thienyl are optionally substituted by up to 2 radicals independently of one another selected from the group of pyridyl, fluorine, chlorine, bromine, $C_1$-$C_4$-alkyl, $C_1$-$C_4$-alkoxy, trifluoromethyl, trifluoromethoxy, benzyloxy and benzyl, where $C_1$-$C_4$-alkyl is optionally substituted by a group of the formula —$NR^3R^4$ in which $R^3$ is $C_1$-$C_4$-alkyl and $R^4$ is hydrogen or $C_1$-$C_4$-alkoxy($C_1$-$C_4$)alkyl, and pyridyl is optionally substituted by $C_1$-$C_4$-alkoxy, $R^1$ is $C_3$-$C_6$-cycloalkyl, $C_1$-$C_4$-alkyl, $C_1$-$C_4$-alkoxy($C_1$-$C_4$)alkyl, benzyl or a group of the formula

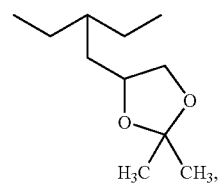

where $C_3$-$C_6$-cycloalkyl is optionally substituted by hydroxy, $C_1$-$C_4$-alkyl or trifluoromethyl, $C_1$-$C_4$-alkyl is optionally substituted by pyridyl, $C_3$-$C_6$-cycloalkyl or hydroxy, and benzyl is optionally substituted by $C_1$-$C_4$-alkoxy, fluorine, chlorine or bromine, $R^2$ is hydrogen, or $R^1$ and $R^2$ together with the nitrogen atom to which they are bonded form a 5- to 6-membered heterocyclyl selected from the group of pyrrolidinyl, piperidinyl, piperazinyl and morpholinyl, which is optionally substituted by up to 2 substituents independently of one another selected from the group of $C_1$-$C_4$-alkyl, hydroxy, cyano, oxo, heteroaryl which is an aromatic, monocyclic radical having 5 to 6 ring atoms and 1 to 3 heteroatoms selected from S, O and N; benzyl; formyl; $C_1$-$C_4$-alkylcarbonyl; and the following groups

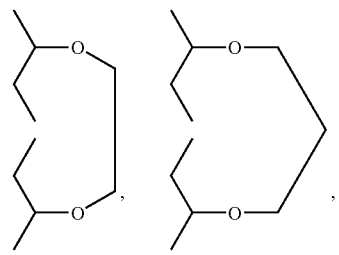

which are linked via the two oxygen atoms to one of the carbon atoms in the heterocycle, where $C_1$-$C_4$-alkyl is optionally substituted by hydroxy or pyridyl, or a salt thereof.

4. A method according to claim 1, where in the compound of formula (I):

A is phenyl, thienyl or a group of the formula

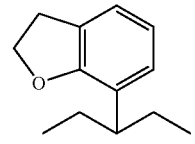

where phenyl is optionally substituted by up to 2 radicals independently of one another selected from the group of pyridyl, fluorine, chlorine, methyl, methoxy, ethoxy, trifluoromethyl, trifluoromethoxy, benzyloxy and benzyl, where methyl is optionally substituted by a group of the formula —NR³R⁴ in which R³ is methyl and R⁴ is hydrogen or 2-methoxyethyl, and pyridyl is optionally substituted by methoxy, $R^1$ is $C_3$-$C_6$-cycloalkyl, methyl, ethyl, propyl, 2-methoxyethyl, benzyl or a group of the formula

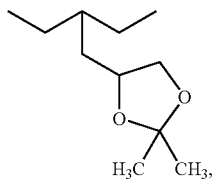

where $C_3$-$C_6$-cycloalkyl is optionally substituted by hydroxy, methyl or trifluoromethyl, methyl, ethyl, propyl is optionally substituted by pyridyl, cyclopropyl or hydroxy, and benzyl is optionally substituted by methoxy, ethoxy, fluorine or chlorine, $R^2$ is hydrogen, or $R^1$ and $R^2$ together with the nitrogen atom to which they are bonded form a 5- to 6-membered heterocyclyl selected from the group of pyrrolidinyl, piperidinyl, piperazinyl and morpholinyl, which is optionally substituted by up to 2 substituents independently of one another selected from the group of methyl, ethyl, propyl, tert-butyl, hydroxy, cyano, oxo, pyridyl, benzyl, formyl, methylcarbonyl, ethylcarbonyl, propylcarbonyl and one of the following groups

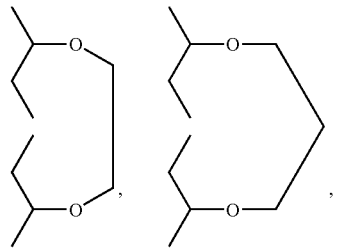

which are linked via the two oxygen atoms to one of the carbon atoms in the heterocycle, where methyl, ethyl and propyl are optionally substituted by hydroxy or pyridyl, or a salt thereof.

5. A method according to claim 1, where the impairment is a consequence of a condition selected from: mild cognitive impairment, age-associated learning and memory impairments, age-associated memory losses, vascular dementia, craniocerebral trauma, stroke, dementia occurring after strokes (post-stroke dementia), post-traumatic dementia, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

6. A method according to claim 1, wherein the impairment is a consequence of Alzheimer's disease.

\* \* \* \* \*